(12) United States Patent
Leupold et al.

(10) Patent No.: US 12,129,457 B2
(45) Date of Patent: Oct. 29, 2024

(54) ILLUMINATION FOR A PHOTOBIOREACTOR

(71) Applicant: Sartorius Stedim Biotech GmbH, Goettingen (DE)

(72) Inventors: Marco Leupold, Kassel (DE); Bernward Husemann, Goettingen (DE); Simon Topp-Manske, Lohfelden (DE); Christian Grimm, Heilbad Heiligenstadt (DE)

( * ) Notice: Subject to any disclaimer, the term of this patent is extended or adjusted under 35 U.S.C. 154(b) by 115 days.

(21) Appl. No.: 16/648,656

(22) PCT Filed: Sep. 6, 2018

(86) PCT No.: PCT/EP2018/074004
§ 371 (c)(1),
(2) Date: Mar. 18, 2020

(87) PCT Pub. No.: WO2019/057508
PCT Pub. Date: Mar. 28, 2019

(65) Prior Publication Data
US 2020/0283710 A1 Sep. 10, 2020

(30) Foreign Application Priority Data
Sep. 19, 2017 (DE) .................... 10 2017 008 769.5

(51) Int. Cl.
*C12M 1/00* (2006.01)
(52) U.S. Cl.
CPC ............ *C12M 21/02* (2013.01); *C12M 23/22* (2013.01); *C12M 31/08* (2013.01); *C12M 31/10* (2013.01)
(58) Field of Classification Search
None
See application file for complete search history.

(56) References Cited

U.S. PATENT DOCUMENTS

| 3,986,297 A | 10/1976 | Ichimura et al. |
| 5,104,803 A | 4/1992 | Delente |
| (Continued) | | |

FOREIGN PATENT DOCUMENTS

| CN | 102296035 | 12/2011 |
| DE | 195 17 039 | 11/1996 |
| (Continued) | | |

OTHER PUBLICATIONS

International Search Report of Dec. 11, 2018.
German Search Report of Aug. 24, 2018.

*Primary Examiner* — Holly Kipouros
*Assistant Examiner* — Nathan G Esperon
(74) *Attorney, Agent, or Firm* — Gerald E. Hespos; Michael J. Porco

(57) ABSTRACT

A container (1, 1b) of a bioreactor (1a, 1b) has a container interior (22) designed for being filled with a medium (8) including a photoreactive material, and designed for at least partially triggering a photochemical reaction of the photoreactive material. The container (1, 1b) has at least one illuminant receiving pouch (11) that is at least partially transparent for an electromagnetic radiation (14), and that is arranged on a illuminant opening (12) within the container interior (22) and is designed to receive at least one illuminant (15, 15a, 15b, 15c, 15d, 15e) from an outer side (A) through the illuminant opening (12, 12a, 12b). The illuminant at least partially irradiates the medium (8) such that the photochemical reaction of the photoreactive material can be triggered by electromagnetic radiation (14) emitted by the illuminant and the illuminant is isolated in relation to the medium (8) by the illuminant receiving pouch (11).

11 Claims, 10 Drawing Sheets

(56) References Cited

U.S. PATENT DOCUMENTS

| | | | | |
|---|---|---|---|---|
| 5,753,106 A * | 5/1998 | Schenck | .................. | C02F 1/325 250/432 R |
| 7,824,904 B1 * | 11/2010 | Dimanshteyn | .......... | C12M 31/12 362/101 |
| 2003/0059932 A1 * | 3/2003 | Craigie | .................. | C12M 21/02 47/1.4 |
| 2005/0078552 A1 * | 4/2005 | Zambaux | .............. | B01F 35/513 366/241 |
| 2007/0048859 A1 * | 3/2007 | Sears | ........................ | C12N 1/12 435/289.1 |
| 2010/0190227 A1 * | 7/2010 | Dauth | .................... | C12M 21/02 423/220 |
| 2012/0282677 A1 * | 11/2012 | Brod | ........................ | C12M 31/12 435/257.1 |
| 2015/0198549 A1 * | 7/2015 | Kjar | ........................ | G01N 27/02 324/649 |
| 2016/0046899 A1 * | 2/2016 | Garnier | .................. | C12M 21/02 435/292.1 |
| 2016/0168521 A1 * | 6/2016 | Mottahedeh | ........... | C12M 23/44 435/257.1 |
| 2017/0175066 A1 * | 6/2017 | Olsen | ........................ | A61J 1/12 |

FOREIGN PATENT DOCUMENTS

| | | | | |
|---|---|---|---|---|
| EP | 2 150 609 | | 11/2010 | |
| EP | 2853584 A1 * | 4/2015 | ............ | C12M 23/28 |
| KR | 20000046481 | * | 7/2000 | |
| KR | 10 2010 0044495 | | 4/2010 | |
| WO | 2010/115655 | | 10/2010 | |
| WO | WO-2010115655 A1 * | 10/2010 | .............. | C12M 1/00 |
| WO | WO-2012077081 A1 * | 6/2012 | .......... | B01F 13/0049 |
| WO | WO-2012098031 A1 * | 7/2012 | ............ | C12M 21/02 |
| WO | WO-2017087790 A1 * | 5/2017 | ............ | C12M 21/02 |

* cited by examiner

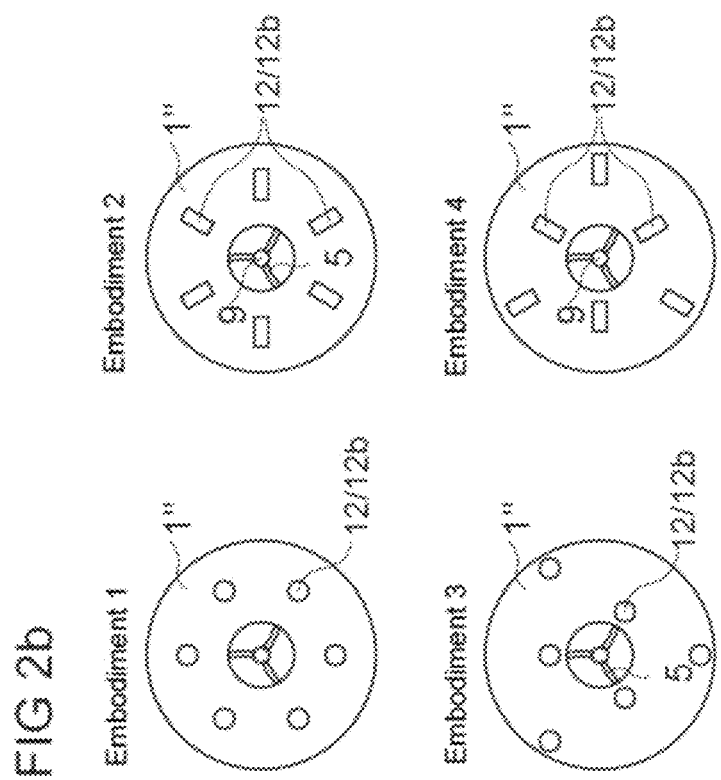
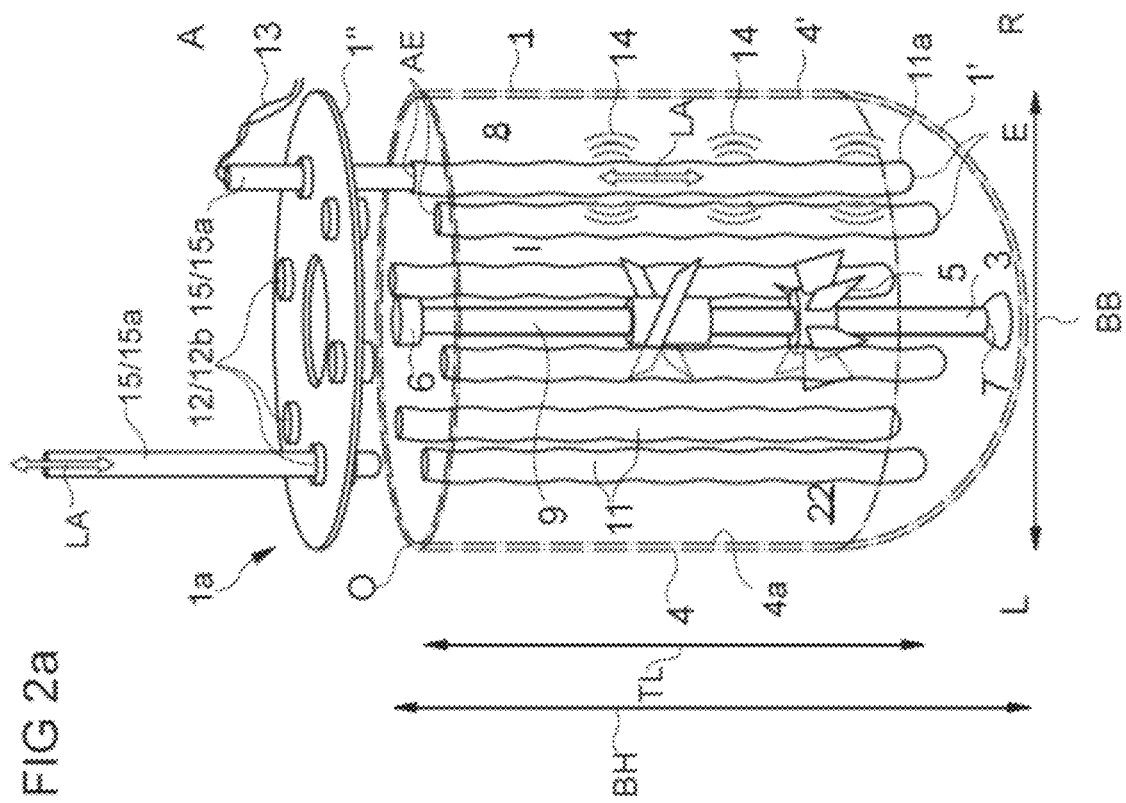

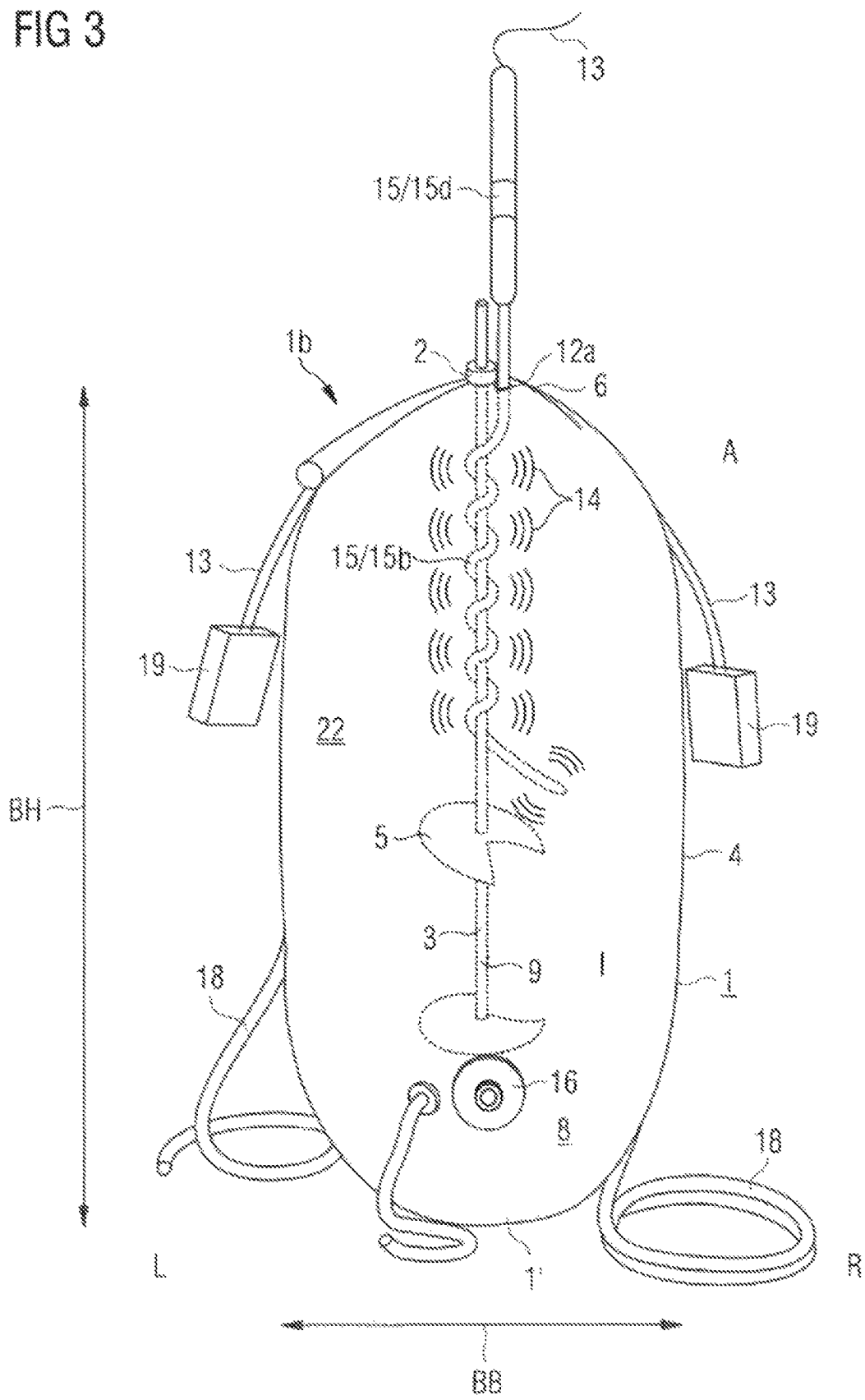

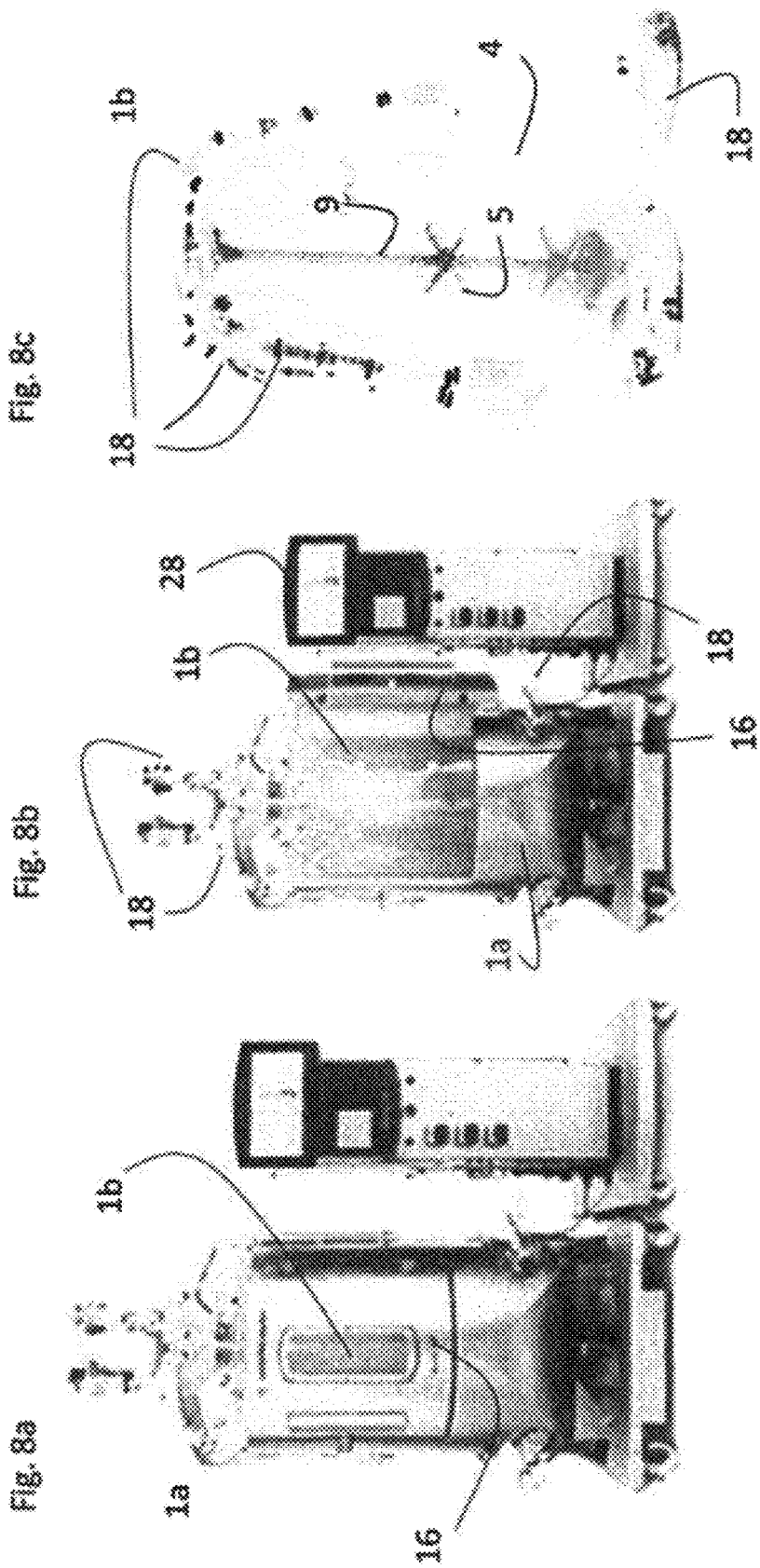

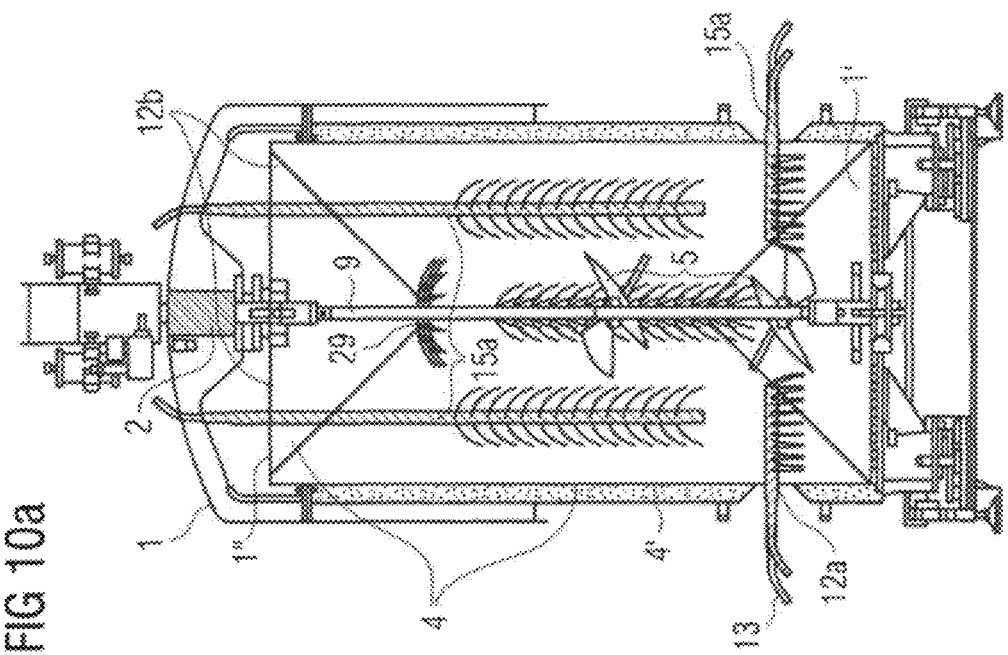
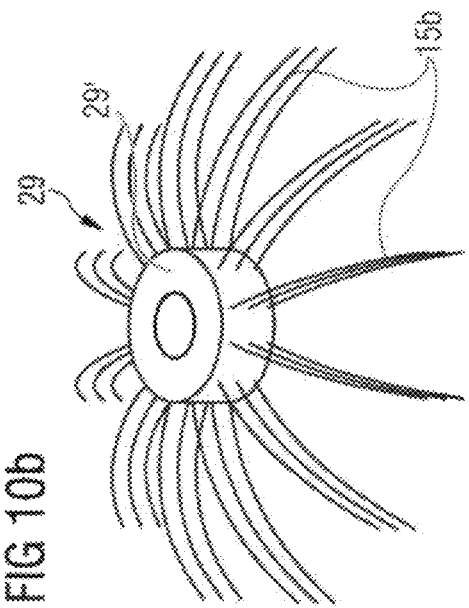
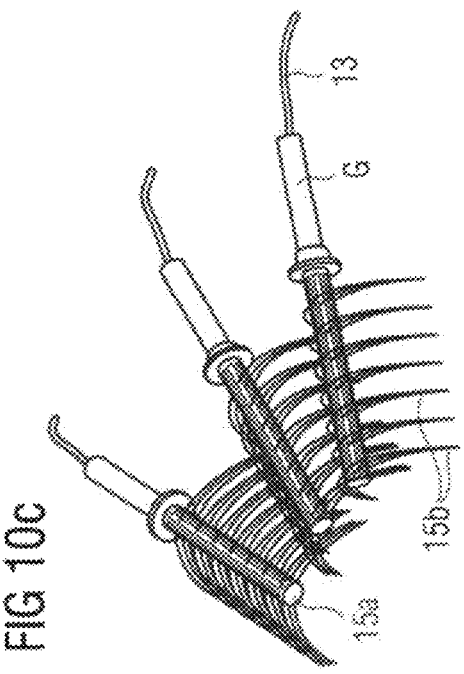

ILLUMINATION FOR A PHOTOBIOREACTOR

BACKGROUND

Summary

The present invention relates to a container, in particular a container of a (photo) bioreactor, preferably a disposable bag, which can receive and/or comprises one or more illuminants for irradiating a medium, in particular a biological medium, with a photoreactive substance. The irradiation or the control of the irradiation of the medium on the inside of the container takes place substantially from the outside, the illuminants or phosphors protruding toward/reaching the inside and irradiating the medium in particular without contact or in a contact-free manner. However, the phosphors can also be in contact with the medium.

In particular, it is substantially a container of a photo bioreactor that is used to store and/or process photoreactive media, for example comprising plants, bacteria, fungi, plant and/or animal cells, living organisms, eukaryotes and/or prokaryotes, while these undergo reactions or processes comprising photo- or light-induced reactions, such as photosynthesis, or processes, especially photo-biochemical and/or biotechnological processes. In particular, so-called photosynthetic active radiation (PAR) is used. Specifically, the light intensity or wavelength of the light can influence the metabolism or the product formation of living organisms.

The invention relates to a disposable bag or a container of a "single-use"/disposable bioreactor, which comprises one or more pockets for receiving one or more illuminants. The pockets, which are mostly referred to below as illuminant-receiving pockets, are designed to receive one or more illuminants such that they can irradiate a medium, in particular a biological medium, located in the container on the inside and thereby trigger or start or initiate a photochemical reaction of the light-sensitive or photosensitive or photoreactive substance.

In general or in all embodiments, a container of a bioreactor, in particular a disposable bag, can comprise a container casing that at least partially or completely surrounds a container interior. In particular, a container casing can comprise a container bottom, a container lid, a preferably barrel-shaped peripheral wall/surface and/or a container door. Illuminant-receiving pockets can be arranged on the container casing.

The invention also relates to a container comprising one or more illuminants, which can be arranged on the container casing such that emitted light from the illuminant or illuminants reaches the inside of the container in order to irradiate a medium there. For example, one or more illuminants is/are arranged on/in a container casing and/or on/in a stirring system and/or on/in a wall of a container door of a container or a container door wall such that they can irradiate a medium located in the container on the inside and thereby trigger or start or initiate a photochemical reaction of the light-sensitive or photosensitive or photoreactive substance.

In particular, the means for illuminating according to the invention can be combined.

The invention can be used in particular in one or more of the following areas: biotechnology, molecular farming, processing of biological/chemical media, phototrophic bioprocess technology, biofuels, biorefinery concepts, nutritional supplements, cosmetics, raw material production, food technology, beverage technology, chemical industry, chemical research, laboratory supplies, medical technology, pharmacy, process chemistry, technical chemistry. In particular, the invention can relate to: photoreactors for large-scale production and/or standard photoreactors for basic research in the laboratory and/or photosynthesis plants and/or plants for the production or growing of plants, in particular algae growing plants or algae farms and/or for the production or growing of bacteria, for example cyanobacteria.

Conventional photo-bioreactors are operated such that a photoreactive substance or a photoreactive medium, which is located in a container inner volume of a container of a photo-bioreactor, is irradiated from the outside by means of a light source through transparent container walls. Such a light source may be the sun, the radiation spectrum of which is particularly suitable on earth for the irradiation of plants and/or algae that carry out photosynthesis. In addition, lamps, such as aquarium lamps or other lamps, which have an emission spectrum similar to that of the sun, can also be used for the artificial irradiation of plants and/or algae. In particular, a photo-synthetic active type of illumination is used.

In order to ensure the most effective irradiation of the medium in a conventional photo-bioreactor, a medium is generally passed through transparent tubes and is irradiated with light from the outside. Alternatively, smaller containers or vessels, such as laboratory bottles on a scale of a few liters with transparent glass walls, are often artificially irradiated from the outside. Due to the fact that the bottles only have a small volume, a light radiated in from the outside, which is radiated in e.g. from one side, can also be absorbed by a medium on the inside of the container opposite to the direction of radiation. In order to create optimum radiation or illumination conditions, the radiation power and/or the density of the absorbing medium and/or the number of lamps used and/or the size or volume of the vessel are generally adjusted.

Small quantities or volumes of media can thus be treated and/or processed in the laboratory or, for example, in greenhouse-like rooms by means of light irradiation. Larger quantities of photoreactive media can, for example, be passed through long, winding transparent tubes. Such tubelines are often arranged outdoors and/or on (house) walls such that, for example, light radiation from the sun is permitted.

Diverse reactions, including photochemical reactions, which occur at different times or substantially simultaneously, require improved bioreactors and/or containers. In particular, such improved bioreactors and/or containers are required which allow the operator or user to adjust parameters, in particular physical parameters, and to control, control and/or regulate processes.

It is therefore the object of the present invention to provide an improved container for irradiation and for triggering at least one photochemical reaction of the content or of the medium contained. This object is solved by the independent claims. The subject matters of the dependent claims represent preferred embodiments.

The invention relates to a container, in particular a disposable bag, and preferably a container/disposable bag of a bioreactor and/or a mixing tank or mixing container with a container interior or volume, designed for at least partial filling with a medium comprising at least one photoreactive substance for at least partially triggering or initiating at least one photochemical reaction of the photoreactive (chemical and/or biological) substance or a chemical by irradiation with light or electromagnetic radiation, comprising:

a container surrounding the container interior and having at least one illuminant opening for introducing at least one illuminant through the container casing into a region of the container interior; and at least one illuminant-receiving pocket, at least partially transparent for electromagnetic radiation, preferably a plurality of illuminant-receiving pockets, which is/are arranged on the at least one illuminant opening at least partially within the container interior and is/are designed to at least partially receive the at least one illuminant, preferably a plurality of illuminants, from the outside or via/from an exterior through the at least one illuminant opening, so that the medium can be irradiated at least partially by the at least one illuminant such that the at least one photochemical reaction of the at least one photoreactive substance can be triggered by electromagnetic radiation emitted by the at least one illuminant or the illuminants, the illuminant(s) being isolated from the medium by the at least one illuminant-receiving pocket(s).

In other words, the illuminant or illuminants, which is or are isolated from the medium by the receiving pocket(s), is/are not in direct contact with the medium, which on the one hand protects the medium from external contamination, but at the same time allows the medium to be irradiated with emitted light from the at least one illuminant.

In other words, a container, in particular a disposable bag, is designed to be at least partially filled with a medium comprising at least one photoreactive substance, suitable for at least partially triggering at least one photochemical reaction of the photoreactive or photochemical substance by irradiation with electromagnetic radiation, comprising:

at least one illuminant-receiving pocket, at least partially transparent for electromagnetic radiation, which is arranged or secured or attached to an illuminant opening of the container casing at least partially within the container interior and is designed to at least partially receive at least one illuminant or a plurality of illuminants from the outside through the illuminant opening, the illuminant-receiving pocket(s) and/or the illuminant opening(s) being designed such that the medium can be irradiated at least partially by means of the illuminant(s) such that the at least one photochemical reaction of the at least one photoreactive substance can be triggered by means of electromagnetic radiation emitted by the illuminant(s), and the illuminant(s) is/are isolated from the medium by the illuminant-receiving pocket(s).

In other words, the invention is substantially a container, which is preferably a disposable container, in particular a disposable bag, but can also be a reusable container. The container comprises a receiving pocket or a plurality of receiving pockets or pockets or illuminant-receiving pockets, which is/are designed to receive one or more illuminants and/or light sources. The illuminant-receiving pockets can substantially protrude toward the inside of the container or into the interior of the container, in particular if the illuminant-receiving pockets have received illuminants. The container can also be, for example, a canister, a steel tank, a barrel or another vessel. A disposable bag can be arranged within a bioreactor, for example.

If the illuminant-receiving pockets have received at least one illuminant, then a medium in the container interior can be irradiated by the emitted light from the at least one illuminant. If the medium comprises a photosensitive or photoreactive substance, for example an algae, a process or a reaction can be triggered or started or initiated by means of the light irradiation of the illuminant when the illuminant is switched on or during operation of the illuminant. For example, in the exemplary case, the algae can be caused to perform photosynthesis. In particular, by irradiation of the photosensitive or photoreactive substance, energy in the form of photons is provided and at least partially absorbed or taken up the photosensitive or photoreactive substance, so that one or more photochemical and/or biochemical and/or physical reactions are triggered. Because the illuminant-receiving pocket is at least partially transparent, in particular for light in the visible wavelength range, light emitted by an illuminant can at least partially pass or propagate through the wall of the illuminant-receiving pocket or through the (illuminant receiving) pocket wall and thus irradiate the volume or medium located in a container interior.

If an illuminant is at least partially received by an illuminant-receiving pocket, the illuminant is preferably located substantially on the inside of the container or in the container interior. Nevertheless, the illuminant is isolated from the medium or from the container interior by the wall of the illuminant-receiving pocket or by the (illuminant receiving) pocket wall, so that there is substantially no direct contact between the medium and the illuminant. In order to differentiate the spaces precisely, an "exclusive container interior" can be defined, which is characterized by containing only the volume of one medium. An "exclusive container interior" does not include the volume that one or more illuminants and illuminant-receiving pockets take up, in particular if the at least one illuminant-receiving pocket has at least partially received at least one illuminant. The container interior or the container volume, on the other hand, should be defined such that it corresponded to the volume the container would have if it did not include an illuminant-receiving pocket(s) and instead a substantially flat container casing, which means that it would not be indented or bulged inward by an illuminant-receiving pocket. In other words, a container interior corresponds to a volume of a container without illuminant-receiving pocket(s), in particular if its container casing does not comprise illuminant openings for illuminant-receiving pockets.

For this reason, if an illuminant is at least partially received in an illuminant-receiving pocket or is at least partially arranged within an illuminant-receiving pocket, it can be located at least partially in the container interior, but substantially not in the exclusive container interior. Eventually, the illuminant is separated or isolated from the medium by the pocket wall or the wall of the illuminant-receiving pocket.

A container can comprise an illuminant-receiving pocket or approximately two, three, four, five, six, seven and in particular up to approximately thirty illuminant-receiving pockets. However, it is not excluded that a container comprises more than thirty illuminant-receiving pockets. A illuminant-receiving pocket can, for example, also receive several illuminants and/or light sources. For example, an illuminant-receiving pocket can receive approximately two, three, four, five, six, seven and more illuminants, in particular a bundle of illuminants, for example optical fibers.

The advantage of a container with illuminant-receiving pockets is that there is no direct contact between an illuminant and a medium, so that the medium is not contaminated with substances from the outside by an illuminant used for the irradiation. In particular, illuminants can also be added, exchanged and/or removed from the outside during a chemical process, so that the irradiation or illumination situation can be adapted to the respective process without the container necessarily having to be opened from outside, which could affect the process flow.

Because the interior of the container is accessible from the outside through the illuminant-receiving pockets but is nevertheless isolated from the outside by the pocket walls of the illuminant-receiving pockets, the illumination situation can be changed without having to open the container interior to the outside, which could lead to an impairment of the process of a medium on the container inside each time. In this way, it can be avoided that physical parameters of the medium or of the container interior are impaired, for example by: a change in temperature, a change in pressure, loss of a substance due to evaporation, contamination by substances, for example bacteria, chemicals, oxygen, etc.

In addition, the adaptation of an illumination or irradiation situation can be carried out in a simple manner in that illuminants can be exchanged, added or removed from the illuminant-receiving pockets accessible from the outside.

Because an illuminant or a light source is not in direct contact with the medium, sterilization of an illuminant can be dispensed with, for example. It may substantially be sufficient to sterilize the container and in particular the container interior in order to ensure that the medium is not contaminated, for example by harmful microorganisms or other substances that could affect a chemical and/or biochemical and/or biological and/or physical process.

According to one aspect, a container comprises an illuminant-receiving pocket or a plurality of illuminant-receiving pockets, at least one illuminant-receiving pocket being rigid and/or having a substantially constant volume or pocket internal volume. In other words, one or more illuminant-receiving pockets are provided on a container or on a container casing, which substantially cannot be compressed, pressed together or squeezed together, particularly when the container is being filled with a medium.

An at least partially rigid design or a substantially constant volume or pocket internal volume of the illuminant-receiving pocket can at least partially prevent an illuminant-receiving pocket from being compressed or squeezed by the medium in the interior of the container if no illuminant is arranged in a pocket inner volume. This has the advantage that an illuminant can also be arranged in a simple manner within the pocket inner volume of the illuminant-receiving pocket if the container inner volume is already filled with a medium. In particular, this can prevent an (illuminant receiving) pocket wall of the illuminant-receiving pocket from being broken or damaged by the illuminant being pushed in.

A constant volume or pocket inner volume can be provided or made possible in that a frame and/or basket-like frame or mesh is arranged on the illuminant-receiving pocket and/or in the pocket inner volume, and/or the (illuminant receiving) pocket wall of the illuminant-receiving pocket includes reinforcements or thickenings of the wall thickness and/or additional materials. In particular, the means by which a substantially constant volume can be achieved is so stable that it cannot be deformed or pressed in under the influence or under the pressure of the medium located in the container interior.

According to one aspect, a container comprises an illuminant-receiving pocket or a plurality of illuminant-receiving pockets, wherein the illuminant-receiving pocket(s) is/are arranged on an illuminant opening or a plurality of illuminant openings positioned on a peripheral wall/surface of the container. In other words, a container casing, in particular a peripheral wall, comprises illuminant openings, in particular at a plurality of locations and preferably distributed along a circumference, through which illuminants and/or light sources can be accommodated by the illuminant-receiving pocket(s) from the outside.

According to one aspect, the container casing of a container comprises a container wall, preferably a barrel-shaped peripheral wall, a container bottom and a container lid that can be removed from the container wall, the at least one illuminant opening being formed in the container lid.

In other words, a container wall, in particular a preferably barrel-shaped peripheral wall of the container casing, and/or a container lid of the container casing can each comprise openings or illuminant openings through which illuminants can be arranged in an illuminant-receiving pocket or inserted into an illuminant-receiving pocket. This is advantageous since the outer sides of a container wall and/or a container lid can be easily accessible from the outside, so that an illuminant can be easily attached or arranged in the container interior for irradiation of a medium. The replacement and removal of an illuminant can also be done easily.

According to one aspect, the container is a disposable container, in particular a disposable container of a bioreactor.

A disposable element, such as a disposable container, in particular a disposable bag, generally has the advantage that it and, in particular, its interior can be made sterile and does not have to be cleaned, sterilized or autoclaved again after use and contamination with contents, but can be disposed of. By using inexpensive materials for the production of disposable bioreactors, processes can be carried out or implemented particularly inexpensively. All components of a container, in particular a bioreactor, as well as all accessories can be designed as disposable elements. Alternatively, partial components of a container, in particular a bioreactor, as well as partial components of an accessory can be designed as disposable elements, whereas other components or elements can be/represent reusable elements.

In particular, on a disposable container, for example a disposable bioreactor, an illuminant-receiving pocket can be at least partially formed from a plastic, in particular from a soft plastic and/or in sections from a metal, for example steel, attached and/or fixed and/or glued and/or be welded on. An illuminant-receiving pocket can in particular comprise a metal if the pocket is to be substantially structurally supported or held in a dimensionally stable manner by a metal structure, for example a basket-like braid. In this way, it can be avoided that an illuminant-receiving pocket deforms, for example in the unfilled state. An illuminant-receiving pocket and a container or disposable bioreactor can be constructed in several pieces, in particular in two pieces, and can be connected, for example, by means of a composite. Alternatively, the illuminant-receiving pocket and the container or disposable bioreactor can be formed in one piece. A preferred embodiment of a container, in particular a disposable bioreactor, for one-way use, can comprise a container wall, illuminant-receiving pockets or also other elements that substantially or at least partially are made of a so-called "soft plastic" or a particularly flexible plastic, in particular a soft PVC and/or polyolefin, in particular polyethylene. Sections serving to stabilize the container structure, however, can be made of a harder material. Such elements and/or sections can be formed in part from a so-called "hard plastic" or from a more rigid or dimensionally stable plastic, in particular from a (meltable) thermoplastic or from a (non-meltable) thermoset, for example a synthetic resin.

According to one aspect, the container is a reusable container, in particular a reusable container of a reusable bioreactor.

In cases in which a particularly large quantity of a medium, for example more than about 500 l, in particular more than about 5000 l, is to be processed and/or stored and/or transported in a container, it is advantageous to use a particularly large container, for example a steel tank. Such containers can prove to be particularly inexpensive in reusable use, for example as reusable bioreactors and/or reusable fermenters and/or reusable mixing systems and/or reusable brewing kettles and/or reusable fermentation systems.

In particular, an illuminant-receiving pocket can be attached and/or screwed and/or fixed and/or glued and/or welded to the container wall of a reusable container or reusable bioreactor. The illuminant-receiving pocket can be formed at least partially from a glass and/or a plastic and/or in sections from a metal. In this way, the illuminant-receiving pocket and the container or reusable bioreactor can be designed in several pieces, in particular in two pieces, and can be connected via a composite and/or other means. Alternatively, the illuminant-receiving pocket and the container or reusable bioreactor can be formed in one piece. It may also be the case that the wall of a reusable container only comprises an opening, to which an illuminant-receiving pocket can be arranged or attached or fixed or fastened. For example, a reusable container could be substantially made of steel, whereas illuminant-receiving pockets, which can be used, for example, for single-use and can be made of a plastic and can be sterilized, can be attached to openings of the reusable container. An illuminant-receiving pocket can also be/represent a hollow and substantially transparent tube, which can be designed for multiple use and can be sterilizable.

According to one aspect, the illuminant-receiving pocket(s) is or are designed to at least partially receive one or more illuminants comprising a light-emitting rod, a light-emitting fiber or a light guide or an optical fiber, a light-emitting diode and/or a light source, in particular a lamp and preferably a tubular lamp and/or a laser from the outside through the illuminant opening. In other words, one of the illuminant-receiving pockets can receive one of said illuminants and/or light sources. Alternatively, one of the illuminant-receiving pockets can receive several of the illuminants and/or light sources mentioned. For example, various illuminants and/or light sources for irradiation of the interior of the container or the medium can also be arranged on or in the container. For example, a light-emitting rod or a light rod and an optical fiber can each be accommodated by the container by means of one or more illuminant-receiving pocket(s). In particular, the illuminant can comprise a light-emitting fiber or a light guide, which is wound or convoluted around an element, for example a rod and/or a line, in particular a line for gas supply and/or discharge and/or a so-called sparger. The element, for example the gas line, which is wrapped with the light-emitting fiber 15b, can already be located in the interior of the container or can be arranged in the interior. The wrapped element can alternatively also be pushed into and/or through an opening, for example into an illuminant-receiving pocket, such that when a light is coupled into the fiber, the light is at least partially emitted along the surface of the element toward the inside of the container.

The illuminant-receiving pockets, which are substantially completely watertight, can prevent illuminants from being damaged, which are generally not used in connection with liquids or under water or within liquids. It is therefore an advantage that the illuminants and/or light sources mentioned can substantially get into a container interior filled with a medium, without these illuminants and/or light sources necessarily having to be watertight. This is particularly advantageous if the medium is a liquid. In the ideal case, there is therefore no need for the illuminants to be particularly suitable for applications under water or in liquids.

According to one aspect, the at least one illuminant-receiving pocket is made of the same material as a large part of the container casing, in particular of a transparent soft plastic, and is preferably formed in one piece with the container casing or the container. Alternatively, the illuminant-receiving pocket and/or the container casing can also be formed at least partially from glass and/or a transparent hard plastic or resin. The container casing and/or the illuminant-receiving pocket can be made at least partially of a substantially transparent glass, for example quartz glass, of a substantially transparent plastic, in particular of an acrylic glass (polymethyl methacrylate, PMMA), a polycarbonate (PC), a polyvinyl chloride (PVC), a polystyrene (PS), a polyphenylene ether (PPO), a silicone, in particular a highly transparent silicone and/or a polyethylene (PE), in particular HDPE or LDPE. Furthermore, any conceivable combination of the mentioned or other materials can be suitable. Materials with light-conducting and/or light-reflecting particles are also suitable.

There is also an advantage in also forming a container casing from a transparent material, since in this way light from the outside, for example sunlight, can at least partially pass or propagate through the container casing. It may also be possible that an illuminant or a light source for irradiating the medium in the interior of the container from the outside is additionally attached or arranged on the outside through the transparent container casing. In particular, the container interior is optimally irradiated or illuminated. This means that the medium is preferably optimally and/or equally or uniformly irradiated at all positions in the container interior.

Since a medium itself can be substantially cloudy or non-transparent or can strongly absorb light of a certain wavelength range, it is advantageous to attach light sources or illuminants at various positions inside and possibly also outside of the container such that the light can pass or propagate through the transparent container casing and/or walls and/or elements.

According to one aspect, the container comprises an illuminant-receiving pocket that can at least partially filter and/or absorb and/or dissipate electromagnetic radiation, in particular thermal radiation or infrared radiation.

The filtering of heat radiation, which can be absorbed by the medium, is advantageous since it can be avoided in this way that a medium is heated too strongly by the radiation if this is to be avoided. Alternatively, this can also be done by dissipating a heated air. Light of a different frequency range can also be at least partially filtered or absorbed by the illuminant-receiving pocket. This could also at least partially prevent excessive UV radiation from entering the interior of the container.

According to one aspect, the container and/or the bioreactor is/are at least partially, in particular completely, sterilizable.

The container and the lamp holder are particularly preferably made of one or more materials that can be sterilized or autoclaved. For example, containers and/or illuminant-receiving pockets can be formed from a polymer. This has the advantage that the container together with the illuminant-receiving pocket can be sterilized before use, so that a medium filled, for example, into the container interior of the container is in particular not contaminated with microbiological material. The sterilization can be carried out before use of a disposable container, in particular a disposable bioreactor. The sterilization can also be carried out before use (and possibly after or between two uses) of a bioreactor.

In particular, the plastic, from which e.g. a disposable container is substantially formed, and all other elements can be largely sterilized, e.g. using beta or gamma radiation. In general, the material used for the production of a container or for the production of a bioreactor can be sterilized by means of thermal sterilization, by means of steam sterilization, by means of hot air sterilization, by means of chemical and/or physical sterilization (e.g. beta or gamma radiation).

The invention further relates to a container, in particular according to one or more of the preceding aspects, with a container interior designed for filling with a medium comprising at least one photoreactive substance and designed for at least partially triggering at least one photochemical reaction of the photoreactive substance, comprising the following elements:

- a stirring element comprising a stirring shaft with a stirring shaft cavity and an at least partially transparent stirring shaft wall, the stirring shaft cavity being able to accommodate an illuminant and the stirring shaft wall being designed such that the illuminant can emit electromagnetic radiation through the stirring shaft wall into the container interior and trigger the photochemical reaction of the photoreactive substance of the medium.

In other words, a container, which is preferably a disposable bag, comprises a stirring element or a stirring device comprising a stirring shaft. The stirring shaft has a stirring shaft cavity and a substantially or at least partially transparent stirring shaft wall. The stirring shaft could substantially also be called a transparent tube. An illuminant, in particular a light-emitting rod, can be arranged in the tube. During operation, i.e. when the illuminant is switched on, a light emitted by the illuminant can therefore propagate or pass through the transparent stirring shaft wall, so that the container interior and the medium therein are irradiated with the photoreactive substance. As a result of the radiation, a photochemical reaction of the photoreactive substance is to be triggered. In particular, the stirring shaft cavity is designed so that an illuminant can substantially be arranged, exchanged and/or removed from the outside within the stirring shaft cavity.

Due to this aspect, a stirring shaft can be used particularly efficiently. On the one hand, the stirring shaft serves to stir or mix the medium, on the other hand, the stirring shaft with the stirring shaft cavity also serves to accommodate an illuminant. Since a stirring shaft is preferably arranged centrally in a container, a medium can therefore be irradiated centrally or from the container inside or from the center of the container inner volume without having to provide an additional surface for attaching the illuminant.

A container or bioreactor or mixing tank particularly efficient with regard to the irradiation of a medium can also comprise a light source or an illuminant in the center of the container interior, in this case within a stirring shaft. Irradiation is particularly efficient when a flow profile of the medium leads past an illuminant to a container casing and an illuminant in the center of the container interior. Ideally, a trajectory of a photosensitive molecule on average runs such that a molecule is illuminated as optimally as possible with regard to the irradiation duration and intensity of an illuminant, so that the required light is absorbed and a photochemical reaction takes place within a certain, in particular within a short time.

Particularly preferred is the situation in which an illuminant can substantially be arranged, exchanged and/or removed within the stirring shaft cavity from the outside. In this way, an illuminant can be replaced or removed, for example, if a process has largely taken place or has ended and the illumination situation is to be adapted. For example, a reaction following the first reaction may require irradiation with light of a different frequency spectrum. This could then be solved by exchanging light sources.

In particular, aspects and features of the inventions can be combined. For example, a container can comprise a transparent stirring shaft with a stirring shaft cavity for accommodating an illuminant and one or more illuminant-receiving pocket(s). The features described below can also be combined with the previous features, unless they are mutually exclusive.

According to one aspect, a container with a container interior, which is designed for filling with a medium comprising at least one photoreactive substance, is designed for at least partially triggering at least one photochemical reaction of the photoreactive substance and comprises the following elements:

- a container casing with a container inner wall;
- a stirring element comprising at least one rotor blade and a stirring shaft; and
- at least one illuminant, which is arranged at least partially on or in the container inner wall, the stirring shaft and/or the rotor blade, and is designed to irradiate the medium at least partially such that the photochemical reaction of the photoreactive substance can be triggered by means of electromagnetic radiation emitted by the illuminant.

The container can in particular be combinable with the preceding aspects and features of another embodiment of a container.

Additionally or alternatively, at least one container can comprise illuminants and/or light sources, which is or can be arranged on at least one component or element of the container. For example, an optical fiber can be wound around a stirring shaft so that light can be emitted into the interior of the container along the stirring shaft. For example, a container inner wall or a container casing inner surface can be provided at least partially or completely with an illuminant. For example, a wall can comprise light-emitting elements or illuminants, in particular organic light-emitting diodes (OLED) or an OLED field, which can be arranged on the wall over a large area. Additionally or alternatively, individual light-emitting diodes can also be attached to the container casing. Additionally or alternatively, light sticks can also be attached to the container casing. Additionally or alternatively, optical fibers can also be attached inside or on the container casing, these optical fibers being able to emit light that enters or propagates, for example, through a transparent container inner wall or container casing inner surface into the container interior. One or more of these optional features have the advantage that a medium in a container interior can be irradiated over the largest possible area. This can also be the case if, for example, the container casing is not transparent.

In an alternative or additional aspect, for example, all illuminants mentioned can also be arranged in or on a rotor blade.

Additionally or alternatively, particles and/or stirring elements, such as magnetic stirrers or agitators, which have fluorescent properties, can also be provided in the container, so that a light can also be transmitted to the medium in this way. It is advantageous here that the stirring elements are swirled with the medium by stirring the medium and thus can cover a distance in the container interior in different regions of the container interior, as a result of which the highest possible proportion of the medium can be irradiated. For example, such particles or stirring elements can also be equipped, in particular coated, with a phosphorizing substance. In this case, the particles can emit light, in particular after the phosphorizing substance has been irradiated with one of the aforementioned light-emitting elements.

It is particularly preferred that a medium is stirred in the container interior such that the medium is irradiated as intensively or as long as possible by the light-emitting elements. For example, a portion of the medium can first be irradiated by a light-emitting element on the container casing inner surface and then, by stirring, enter an area where it is irradiated by light-emitting elements of a stirring shaft. By attaching light-emitting elements at suitable positions and selecting a specific stirring speed or number of revolutions of the rotor blades and achieving a specific flow profile, an optimum exposure time or illumination time or irradiation time can be achieved for a molecule on average. This means that, for example, a photoreactive molecule in a medium is irradiated so long and intensively (in one piece or without interruption) on average by one or more light-emitting elements that a photochemical reaction is triggered or promoted or initiated.

According to one aspect, the container comprises an illuminant or light-emitting means and/or a light source or light-generating means, wherein an illuminant comprises a light-emitting rod, a light-emitting fiber or a light guide, a light-emitting diode and/or a light source, in particular a lamp and preferably a tubular lamp.

It is advantageous to provide light-emitting elements emitting light over a large area, such as, for example, light-emitting fibers or tubular lamps or LEDs or OLEDs distributed over a large area, since the largest possible volume can be irradiated by means of the emitted radiation.

For example, it may also be the case that an intensity of the irradiation or a quantity of the emitted light or an output of the individual light-emitting elements can be varied or adapted as required. In addition, some or a portion of the light-emitting elements can also be switched on or off, while another part remains switched on or off. The medium can also be irradiated in a pulsed or stroboscopic manner. In particular, however, the medium is irradiated continuously or over a longer period of time or at a longer interval in order to trigger the highest possible reaction rate or as many photochemical reactions as possible.

According to one aspect, the container inner wall or the container casing inner surface comprises a container inner wall structure designed to form an area that is enlarged with respect to an unstructured smooth container casing inner surface, and wherein the illuminant is arranged on or in the container inner wall structure and/or the container inner wall structure can influence or specify a flow profile of the medium. A flow profile of the medium occurs in particular when a medium is stirred or mixed in a container by means of a stirring device.

Due to the substantially structured, in particular corrugated and/or jagged and/or rugged and/or indented and bulged shape of a container casing inner surface, a particularly large area can be provided on the container inside, on which as many light-emitting elements as possible or light-emitting elements emitting light over a large area can be attached. In particular, a light-emitting element emitting light over a particularly large area, for example a pad or field or array, in particular a light-emitting film comprising one or more OLED elements, can be attached to the structured inner wall of the container.

In addition, a structured container casing inner surface (in particular a mixing and stirring tank or a mixing and stirring container) can cause turbulent flows of the flowing or stirred medium, particularly in the vicinity of the structured container casing inner surface. Turbulent flows can cause part of the medium to remain in the vicinity of a light-emitting container casing inner surface for a longer period of time and, for example, to flow past the container casing inner surface several times due to a circular flow profile. This has the advantage that a container casing inner surface or a section of the structured container casing inner surface, which comprises an illuminant, can substantially irradiate a certain part of the medium over a longer period of time (and/or repeatedly). As a result, the likelihood of a photochemical reaction of a photosensitive substance in the medium increases.

Particularly preferred is the situation in which a structured container casing inner surface comprising an illuminant causes, effects or triggers a certain advantageous flow profile of the medium. A certain flow profile of the medium would be advantageous if the flow rate led to a certain part of the medium being in the vicinity of an illuminant for an optimal period of time for triggering a photochemical reaction. At the same time, however, the medium in the tank or container should be thoroughly mixed or stirred so that the largest possible volume of the medium, in particular the entire volume or the highest possible number of photoreactive molecules of the medium, is irradiated by one or more illuminants long enough so that the desired photochemical reaction of as many molecules as possible is triggered. This works particularly well if a plurality of illuminants are fitted within the interior of the container, for example one illuminant on the inner surface of the container casing and, at the same time, another illuminant on a stirring shaft. In this case, a flow profile describing a flow of the medium from one illuminant to another illuminant is preferred. This can be done in particular by means of an optimally designed container inner wall structure.

It should be noted that the term "a certain part of the medium" is not a closed variable, since the part of the medium substantially experiences permanent mixing with other parts or volumes of the medium during the flow. This means, for example, that on average several molecules stay within a certain volume at the same time somewhat longer in a turbulent flow than in a laminar flow, since the flow substantially flows in a circle or the flow profile is substantially circular.

For a molecule that is undergoing or experiencing a photochemical reaction, i.e. substantially changing from an educt to a product by exposure to light, there is an ideal uninterrupted irradiation duration, which depends, among other things, on the irradiation intensity. The irradiation intensity in turn depends on the power of an illuminant and the distance between the molecule and the illuminant at which a light of a specific power is emitted. Furthermore, the irradiation intensity also depends on how dense the medium is or how many absorbent molecules are present in the medium. In the event that the medium is very dense, less light can reach more distant areas of the container interior, so that a molecule may only be exposed to a sufficiently high level of irradiation if it has been in the vicinity of an illuminant for long enough.

Particularly preferred is container (in particular a mixing tank or mixing container) that is designed to irradiate as many molecules of a photoreactive substance as efficiently as possible, i.e. within the required or optimal irradiation time, such that the photochemical reaction is triggered. As already mentioned, in particular a flow profile in connection with an illumination situation (position of the light sources/illuminants, radiation power, absorption and density of a medium) can be given, for example, by optimizing a container inner wall structure and a stirring device or mixing device in this respect.

The optical density, in particular the extinction, including absorption and scattering, represent physical quantities on which it can depend how efficient light irradiation with regard to the reaction rate is. A very (optically) dense medium, which in particular strongly absorbs light of at least part of the frequency range, can therefore strongly filter or absorb a color or a frequency range of the light within a short path of the light traveled. For this reason, a molecule at a greater distance from the light-emitting means or the illuminant can no longer be adequately irradiated with the light of a specific frequency or wavelength the molecule would require so that a photochemical reaction can be triggered. For these reasons, in particular to ensure efficient irradiation, a mixing device could be provided, which is designed so that also the molecules at a greater distance from the light-emitting means get closer to it in order to be irradiated there sufficiently and for a long time. In this case, it can also be advantageous to adapt the position, the power and the number of light-emitting means, as well as the stirring or mixing speed of the medium. Alternatively, however, the medium can also be diluted, so that fewer molecules are present in a container and therefore less light is absorbed at a short distance from an illuminant.

According to one aspect, a container comprises a tube that is transparent or translucent for electromagnetic radiation and is designed to store and/or guide a medium, wherein the medium can be irradiated, for example, from the outside through a transparent tube wall. In other words, a medium can flow through a transparent tube of a container, wherein the medium can be irradiated from the outside by an illuminant through the transparent or translucent tube wall. In particular, the medium in the tube can be irradiated from the outside by the sun. Such a tube could, for example, be/represent an inlet and/or an outlet and/or a bypass of the container or the bioreactor.

In addition, the invention relates to a method for at least partially triggering or starting or initiating at least one photochemical reaction of a photoreactive (chemical and/or biological) substance in a medium, comprising the following steps:
  arranging or attaching or securing or fixing at least one illuminant-receiving pocket at least partially transparent to electromagnetic radiation or light on an illuminant opening and at least partially within the container interior;
  at least partially receiving an illuminant through the illuminant-receiving pocket from an outside through the illuminant opening or at least partially arranging or inserting an illuminant into the illuminant-receiving pocket from an outside through the illuminant opening;
  filling a container interior of a container, in particular a container of a bioreactor and preferably a disposable bag, with the medium comprising or including the photoreactive (chemical and/or biological) substance;
  isolating or sealing or separating the illuminant by the illuminant-receiving pocket, in particular by a substantially (water/solvent) tight pocket wall of the illuminant-receiving pocket against the medium; and
  at least partially irradiating or illuminating or lighting the medium with the illuminant such that the photochemical reaction of the photoreactive substance is at least partially triggered by means of electromagnetic radiation emitted by the illuminant.

The invention also relates to a method for at least partially triggering at least one photochemical reaction of a photoreactive substance in a medium, comprising the following steps:
  arranging or attaching or securing or fixing at least one stirring element comprising at least one stirring shaft with a stirring shaft cavity and an at least partially transparent stirring shaft wall at least partially within the container interior;
  arranging at least one illuminant at least partially within the stirring shaft cavity;
  filling a container interior of a container, in particular a container of a bioreactor, with the medium;
  at least partially irradiating the medium with the illuminant through the stirring shaft wall such that the photochemical reaction of the photoreactive substance is triggered by means of electromagnetic radiation emitted by the illuminant.

As already mentioned, such features characterizing the two methods can be combined with one another. In particular, synergy effects can result from a suitable combination. Intensive and large-area radiation of the container interior with light is particularly preferred, which is why a combination of both methods is possible. In particular, a high reaction rate can be achieved with respect to the at least one photochemical reaction of the respective molecules.

Preferably, an illuminant or a light source is initially received by an illuminant-receiving pocket in one step, so that the illuminant is at least partially located within the substantially not yet filled container interior. Subsequently, in a later step, the container interior can preferably be filled with a medium. If you first filled the interior of the container with a medium, it could be difficult to arrange an illuminant in the illuminant-receiving pocket, since the illuminant-receiving pocket could be compressed or squeezed by the medium, so that when the illuminant is being pushed into the illuminant-receiving pocket, the wall of the illuminant-receiving pocket could be damaged or broken. However, it cannot be ruled out that a method will take place in the latter order. However, this means that an illuminant should be pushed into the illuminant-receiving pocket very carefully or that the illuminant-receiving pocket should substantially or at least partially be rigid. Thus, an inner volume of an illuminant-receiving pocket or a pocket inner volume can be at least partially preserved even when the container interior is filled, so that the reception of an illuminant is favored.

The invention will be explained in more detail below on the basis of embodiments shown in the figures. Individual features shown in the figures can be combined with other embodiments, provided that they are not mutually exclusive. The same reference numerals designate the same or similar components of the embodiments.

BRIEF DESCRIPTION OF THE DRAWINGS

FIG. 2a is a schematic exploded view with a view into a container of a bioreactor with a mixing device, a container lid and illuminant-receiving pockets on the container lid according to a further embodiment.

FIG. 2b shows four schematic top views of the container lid of a container of a bioreactor with a mixing device, container lid and illuminant-receiving pockets on the container lid according to further embodiments.

FIG. 3 is a schematic side view with a view into a disposable container of a bioreactor or disposable bag with a mixing device and light guide on the stirring shaft according to a further embodiment.

FIG. 8a is a front view of a bioreactor with a steel casing, which contains a disposable bag in its inner volume, according to a further embodiment.

FIG. 8b is a frontal view of an opened bioreactor with a steel casing, which contains a disposable bag visible in its inner volume, according to the embodiment of FIG. 8a.

FIG. 8c is a frontal view of a disposable bag that can be received by the bioreactor with the steel casing according to the embodiment of FIGS. 8a and b.

FIG. 10a is a schematic side view with a view into a disposable container of a bioreactor with a mixing device and light sticks with light guides according to one embodiment.

FIG. 10b is an attachment device for light guides according to an embodiment.

FIG. 10c shows light sticks with light guides according to one embodiment.

DETAILED DESCRIPTION

Figure 1:
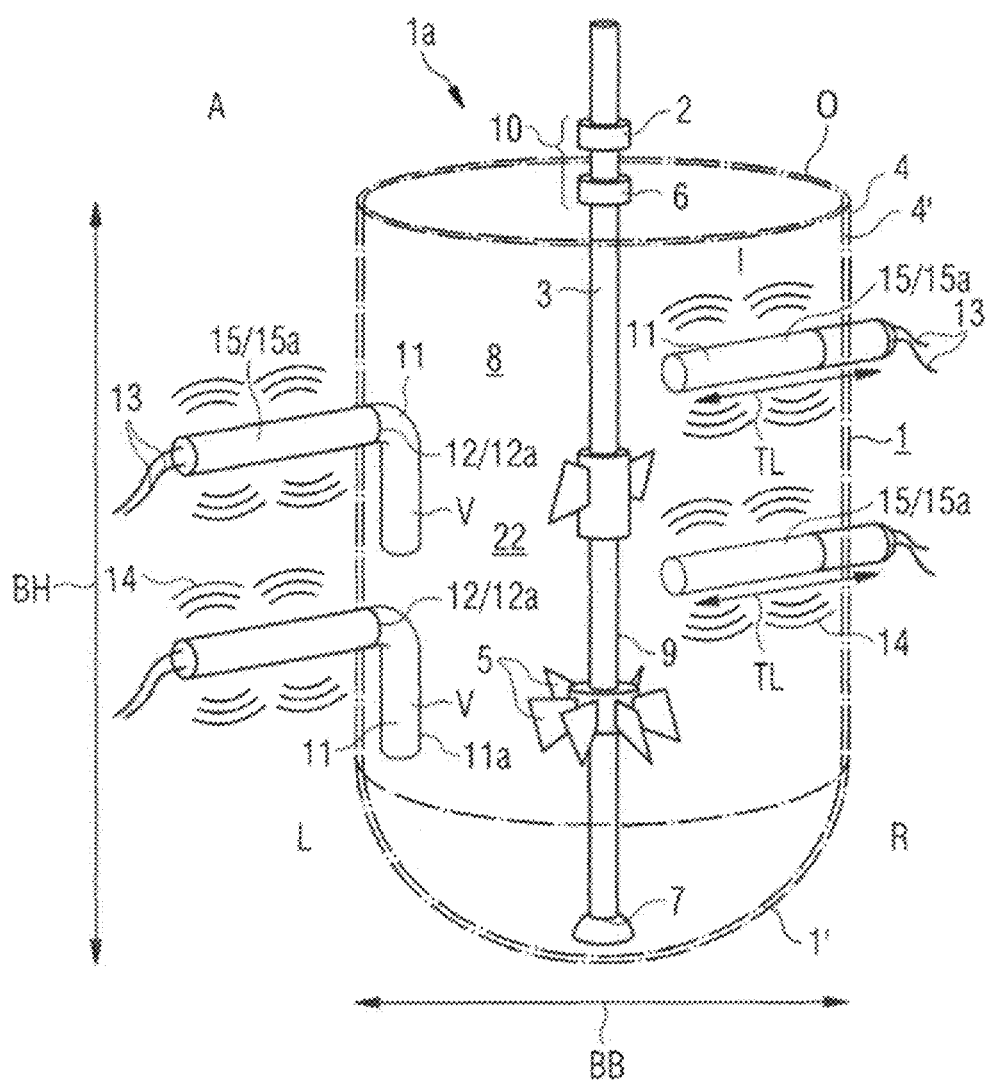
FIG. 1 is a schematic side view with a view into a container of a bioreactor with a mixing device and illuminant-receiving pockets on the container casing according to one embodiment.

FIG. 1 shows a side view of an embodiment of a container of a bioreactor 1a comprising a container 1 with a container bottom 1', an upper edge O and a container casing 4. Furthermore, the container of the bioreactor 1a has one or more illuminant openings 12, in particular one or more illuminant opening(s) in the container wall 12a, and one or more illuminant-receiving pockets 11. Since the container of the bioreactor 1a is designed to receive one or more illuminants 15, the bioreactor 1a can also be referred to as a photo bioreactor. An illuminant 15 can also be referred to as a light-emitting means or light-emitting element.

In addition to the container 1, the bioreactor 1a in FIG. 1 further comprises a drive 10 which has a motor, for example a three-phase motor, a stepper motor, a pneumatically driven motor and/or the like. The mixing system arranged in the container 1 has a mixing device that is designed and provided to at least partially mix a medium 8 arranged or filled in the container 1. The medium 8 can comprise a fluid and/or a solid and/or a gas and can in particular be designed as a fluid mixture and/or a solid mixture or batch, or also as a mixture of at least one fluid and at least one solid. A medium 8 can in particular be a biological medium or a chemical medium.

Furthermore, two illuminants 15 are partially received by the illuminant-receiving pockets 11 on the left side L and two illuminants 15 are substantially completely received by the illuminant-receiving pockets 11 on the right side R. In the present embodiment, the illuminants 15 are designed as light-emitting rods or elements 15a, which can emit electromagnetic radiation 14 or light, in particular when switched on.

The embodiment of FIG. 1 is to be understood such that all or only some of the light-emitting rods 15a are in each case completely or partially or not at all received by the illuminant-receiving pockets 11. The embodiment of FIG. 1 is also to be understood such that the container 1 or the container interior 22 can be unfilled or at least partially or completely be filled/filled up with a medium 8. In other words, this embodiment relates substantially to the structural properties of the container 1 or the bioreactor 1a, whereas the light-emitting rods 15a can only be attached to the container 1 and/or a medium 8 can be filled into the container 1.

The two illuminant-receiving pockets 11 on the left-hand side L have only partially received the respective two light-emitting rods 15a and, because they are substantially not yet (completely) filled with the light-emitting rods 15a, hang downward in the direction of the container bottom 1'. This state can be considered or referred to as the "unfilled state" of the illuminant-receiving pockets 11.

The illuminant-receiving pockets 11 or their (illuminant receiving) pocket walls, which are also referred to as pocket walls 11a, can be made of a soft, flexible and/or possibly of an expandable plastic. According to FIG. 1, the light-emitting rods 15a on the left side L can be inserted or pushed into the pocket inner volume V of the pocket inside of the illuminant-receiving pockets 11 from the outside A, which are located on the container inside I or in the container interior 22.

By contrast, the two illuminant-receiving pockets 11 on the right-hand side R have substantially completely received the respective two light-emitting rods 15a, which is why they protrude substantially perpendicular to the container casing 4 or horizontally on the inside I or into the container interior 22 of the container 1. This state can be considered or referred to as the "filled state" of the illuminant-receiving pockets 11, since the pocket inner volume V on the pocket inside of the illuminant-receiving pockets 11 is substantially completely filled by the light-emitting rods 15a. In this case, the respective light-emitting rod 15a on the right side R was pushed into or inserted or received in the pocket inner volume V of the pocket inside of the respective illuminant-receiving pocket 11 via the respective illuminant opening in the container wall 12a from the outside A, which pocket 11 is located on the container inside I or in the container interior 22. In this state, the respective light-emitting rod 15a can at least partially emit a light or an electromagnetic radiation 14 onto the container inside I or into the container interior 22, the respective light-emitting rod 15a only being substantially isolated from the medium 8 by a (illuminant receiving) pocket wall 11a, also called pocket wall 11a.

In the present embodiment of FIG. 1, four illuminant-receiving pockets 11, illuminant openings in the container wall 12a and light-emitting rods 15a are provided. In an alternative embodiment, however, only one illuminant-receiving pocket 11 and one illuminant opening in the container wall 12a or any other number of illuminant-receiving pockets 11 and illuminant openings in the container wall 12a can be provided. In an alternative embodiment, another illuminant 15, for example an optical fiber or a lamp, can be received by the illuminant-receiving pockets 11 instead of a light-emitting rod 15a.

The light-emitting rods 15a can be supplied with energy or current or voltage, for example, in the switched-on state or in operation by means of a battery or rechargeable battery and/or via a line 13, in particular via a power cable with mains plug.

In the embodiment shown, the container 1 of the bioreactor 1a is a tank, which can be a steel tank, for example, and is penetrated by a stirring element 3, which is arranged on the container inside I of the container 1 and can penetrate the container 1 from one end to the other opposing end completely.

Furthermore, the bioreactor 1 has a drive device 2, which is arranged substantially outside the container 1. The stirring element 3 is coupled to the drive device 2. The stirring element 3 has a stirring shaft 9 that is substantially rod-shaped. The stirring shaft 9 is arranged substantially completely inside (on the container inside I) of the container 1 and can either protrude into the container 1 from one end of the container 1 or penetrate the container 1 completely from a first end of the container 1 to a second end of the container 1, in particular from a container lid (not shown here) to a container bottom 1'. In the embodiment shown, the stirring shaft 9 is supported on two opposite ends of the container 1. The stirring shaft 9 is supported on a drive-side bearing 6 and on a counter-bearing 7 on the container bottom 1'. In the embodiment shown in FIG. 1, the drive-side bearing 6 is arranged directly adjacent to the drive device 2, while the counter-bearing 7 is arranged on the side of the container 1 opposite the drive device 2 or on the container bottom 1'. A plurality of stirring extensions 5 are formed on the stirring shaft 9, which move through the medium 8 upon rotation of the stirring shaft 9 about an axis of rotation of the stirring element 3 and thereby mix the medium 8. A stirring extension 5 can substantially also be referred to as a rotor blade.

The container 1 or the bioreactor 1a can alternatively also be designed without a stirring shaft 9 and/or without a drive device 2 and/or without a drive-side bearing 6 and/or without a counter-bearing 7 and/or without a stirring element 3, in particular without any element of the mixing device which is used for mixing of the medium 8.

The container 1 thus has a container interior 22 on the container inside I, which can be completely or partially filled with a medium 8. In particular, the container 1 can be at least partially or completely filled at the time of irradiation of a medium 8 with electromagnetic radiation 14. In particular, the medium 8 is stirred or mixed during the irradiation. For irradiation, in particular all of the illuminant-receiving pockets 11 can be at least partially filled with the respective illuminants 15. However, only a part of the illuminant-receiving pockets 11 can be at least partially filled with the respective illuminants 15.

In particular, the illumination situation (illumination intensity or power, illumination position, emitted spectrum) can be adapted to the circumstances by adding, removing and/or replacing an illuminant 15. In addition, the light-emitting area of the illuminant 15 can be varied by only partially or completely projecting or pushing an illuminant 15 into the illuminant-receiving pocket 11.

In the event that a container interior 22 is at least partially filled with a medium 8, but no illuminant 15 is arranged in at least one illuminant-receiving pocket 11, the illuminant opening in the container wall 12a of the container casing 4 can be closed with a lid (not shown here), so that the medium 8, for example a liquid, does not push the corresponding unfilled illuminant-receiving pocket 11 outwards or to the outside A. The lid or closure can substantially prevent an illuminant-receiving pocket 11 from escaping toward the outside A.

In the present embodiment according to FIG. 1, no container lid is initially shown. Nevertheless, the container 1 can be closed by means of a container lid.

The illuminant-receiving pockets 11, which are arranged on the inside of a container casing and are designed to each receive a light-emitting rod 15a, can in particular have a pocket length TL of approximately 0.1 m to approximately 2 m, preferably approximately 0.3 m to about 1.5 m, and particularly preferably about 0.5 to about 1 m. The diameter of the illuminant-receiving pocket 11 can generally be between approximately 5 cm and approximately 50 cm, preferably between approximately 8 cm and approximately 30 cm and in particular between approximately 10 cm and approximately 20 cm. The ratio between the diameter and the pocket length TL can be, for example, in the case of illuminant-receiving pockets 11 for receiving light guides 15b, approximately 1:5000 to approximately 1:10, in particular approximately 1:1000 to approximately 1:50 and preferably approximately 1:300 to 100. The ratio between the diameter and the pocket length TL can be, for example, in the case of illuminant-receiving pockets 11 for receiving light-emitting rods 15a, about 1:500 to about 1:1, in particular about 1:100 to 1:10 and preferably about 1:50 to 1:20. The pocket length TL and the diameter can substantially be selected depending on the size of the reactor or the container 1, in particular depending on the container width BB and the length and diameter of the light-emitting rods 15a.

The illuminant-receiving pockets 11, which are designed to receive another light-emitting element or illuminant 15, can have different pocket lengths TL. An illuminant-receiving pocket 11 for receiving a light guide can have, for example, a pocket length TL of approximately 1 m to approximately 10 m, in particular approximately 1.5 m to approximately 8 m, and particularly preferably approximately 2 m to approximately 7 m.

The container width BB can in particular be approximately 0.3 m to approximately 3 m, preferably approximately 0.5 m to approximately 2 m, and particularly preferably approximately 0.8 m to approximately 1.5 m.

The container interior 22 of a container 1 of a bioreactor 1a can, for example, assume values between approximately 15 ml and approximately 30,000 liters, in particular between approximately 5 liters and approximately 8000 liters and preferably between approximately 100 liters and approximately 1000 liters.

The values mentioned here as examples also do not exclude dimensions outside these dimensions. The values mentioned can in particular also be adopted for other embodiments.

Aspects and features mentioned as combinable features with respect to other embodiments but not explicitly with respect to this embodiment of FIG. 1 can also be explicitly combined with this embodiment, provided that they are not mutually exclusive with other aspects from the context.

Another embodiment of a container 1 of a bioreactor 1a is shown in the exploded view in FIG. 2a. The container 1 of the bioreactor 1a comprises a container lid 1" that can be detached or removed from the container 1 or from the upper edge O of the container 1 and can be attached. The container lid 1" comprises illuminant openings 12, in particular illuminant openings in the container lid 12b, to each of which an illuminant-receiving pocket 11 can be attached or is attached. In a state attached to the illuminant openings in the container lid 12b, the illuminant-receiving pockets 11 then hang down substantially perpendicularly from the container lid 1" into the container interior 22 toward the container bottom 1'.

An illuminant 15 on the left-hand side L, which in this embodiment is a light-emitting rod 15a, is aligned or arranged relative to the container lid opening 12b, but is substantially not received by the illuminant-receiving pocket 11. It might be that, in this position, the illuminant 15 is just being pushed into or removed from the pocket inner volume V of the illuminant-receiving pocket 11 on the left-hand side L. To this end, the light-emitting rod 15a has to be moved along its longitudinal axis LA substantially perpendicular to the container lid 1" through the illuminant opening in the container lid 12b into the container interior 22 toward the container bottom 1".

An illuminant 15 on the right-hand side R, which in this embodiment is also a light-emitting rod 15a, is aligned or arranged relative to the illuminant opening in the container lid 12b and is substantially completely received by the illuminant-receiving pocket 11. The longitudinal axis LA of the light-emitting rod 15a is arranged or aligned substantially parallel to the container casing 4 or the container inner wall or the container casing inner surface 4a on the container inside I. In other words, a light-emitting rod 15a extends from the container lid 1" toward the container bottom 1', in particular up to the container bottom 1' within the pocket inner volume V of the illuminant-receiving pocket 11, which is located in the container interior 22. In particular, a light-emitting rod 15a extends from the container lid 1" or the reception entrance AE of the illuminant-receiving pocket 11 toward the container bottom 1' to the end E of the illuminant-receiving pocket 11.

If a light-emitting rod 15a at least partially protrudes into the container interior 22 and is isolated from the medium 8 only by the pocket wall 11a, the medium 8 can be irradiated by the electromagnetic radiation 14 emitted by the light-emitting rod 15a in the switched-on condition or in operation. If necessary, light-emitting rods 15a or other illuminants 15 can be added, removed and/or exchanged in order to adapt the illumination situation to a process, for example. Irradiation intensity or power can also be varied. The light-emitting rods 15a can be supplied with current or voltage or energy, for example, via a line 13, in particular via a power cable.

In particular, the mixing device comprising a drive device 2, a stirring element 3, rotor blades 5, a drive-side bearing 6 and a counter bearing 7 and a stirring shaft 9 can be operated such that a medium 8 is mixed or stirred. In this way, a flow profile of the medium 8 can be generated, with the result that an arbitrary molecule of the medium 8 experiences on average a necessary irradiation of an uninterrupted irradiation duration by the illuminants 15, which triggers a photochemical reaction.

The illuminant opening in the container lid 12b and the illuminant-receiving pockets 11 can be distributed, for example, radially symmetrically or not symmetrically along the circumference of the lid edge. FIG. 2b is a view of various embodiments of the container lid 1", embodiments 1 to 4. According to embodiments 1 and 2, illuminant openings in the container lid 12b as well as the illuminant-receiving pockets 11 are distributed at substantially equal intervals, radially symmetrically around the center of the container lid 1" substantially along the circumference of the lid edge. In embodiment 1, all illuminant openings in the container lid 12b are substantially circular, whereas in embodiment 2 all illuminant openings in the container lid 12b are formed or designed to be substantially rectangular. According to embodiments 3 and 4, illuminant openings in the container lid 12b and the illuminant-receiving pockets 11 are not distributed at substantially equal intervals, not radially symmetrically around the center of the container lid 1" substantially along the circumference of the lid edge. For example, it may also be possible for a container lid 1' to comprise illuminant openings 12b that are circular and others that are rectangular. Depending on which shape is predetermined by the illuminants 15 and which illumination situation is desired or required, arbitrary combinations of shapes and position distribution of the illuminant openings can be provided in the container lid 12b.

In the views of FIG. 2b, three rotor blades 5 and a central stirring shaft 9 can also be seen. These can be seen in particular when the container lid 1" is substantially transparent or has an opening at the respective point. For example, such an opening could be used to add a substance into the medium 8 or into the container interior 22.

The embodiments of the bioreactors 1a or containers 1 are preferably designed to be at least partially, in particular completely, sterilized. At least the container interior 22, as well as elements of the bioreactor 1a arranged in the container interior 22 or are to be arranged, are preferably designed to be at least partially, in particular completely, sterilized. The bioreactors 1a can also be designed to generally form a closed system. In other words, opening of such bioreactors 1a can be dispensed with in most cases, in particular in all cases, in particular when a medium 8 is undergoing a process or one or a plurality of reactions. However, a container 1 can be opened, in particular for the purposes of sterilizing the container interior 22.

The illuminant-receiving pockets 11, which are arranged on an inside of a container lid and are designed to each receive a light-emitting rod 15a, can in particular have a pocket length TL of approximately 0.1 m to approximately 5 m, preferably approximately 0.3 m to about 3 m, and particularly preferably about 0.5 to about 2 m. The pocket length TL can substantially be selected according to the size, in particular according to the container height BH of the reactor or the container 1 and the length of the light-emitting rods 15a.

The container height BH can in particular be approximately 0.5 m to approximately 5 m, preferably approximately 1 m to approximately 3 m, and particularly preferably approximately 1.5 m to approximately 2.5 m.

The values mentioned here as examples do not exclude dimensions outside these dimensions. The values mentioned can in particular also be adopted for other embodiments.

Aspects and features mentioned as combinable features with respect to other embodiments but not explicitly with respect to the embodiment of FIGS. 2a and 2b can also be explicitly combined with this embodiment, provided that they are not mutually exclusive with other aspects from the context.

The embodiment of FIG. 3 relates to a single-use (SU) or disposable bag 1b. Since the single-use (SU) or disposable bioreactor/disposable bag is designed to receive one or more illuminants 15, it can also be referred to as a single-use (SU) or disposable photo bioreactor. The disposable bag can be maintained or supported, for example, by means of a frame or a scaffold (not shown here). The disposable bag 1b can also be arranged within a bioreactor or part of a bioreactor.

A light source 15*d*, preferably in the form of a laser, which generates light or electromagnetic radiation 14, which is transported through a light guide 15*b* into the container interior 22 and emitted there, is provided in this embodiment. The light guide 15*b* is guided through an illuminant opening in the container wall 12*a* from the outside A to the container inside I. Furthermore, the light guide 15*b* is attached to a stirring shaft 9 or wound around a stirring shaft 9. The light source 15*d* or the laser is connected to the mains via a line 13, in particular a power cable, and receives the energy required for operation via the cable.

In particular, the light guide 15*b* is designed such that it emits or can emit light 14 over its entire length or at least over a portion of its length on the surface thereof. This substantially depends on the fact that a light is coupled into the light guide 15*b* such that the total reflection condition is not fulfilled or the angle at which the light 14 is reflected does not correspond to the total reflection angle. In this way, a fraction of the total guided light 14 is emitted to the surrounding medium 8 or the container interior 22 with each reflection.

The light guide 15*b* can be wound around a non-rotating part of a stirring shaft 9, for example around an outer rigid guide tube, or be arranged or attached to it in any other form. In particular, the light guide 15*b* can be wound about 5 to about 500 times, preferably about 10 to about 300 times, and particularly preferably about 15 to about 100 times around the stirring shaft 9. Alternatively, it may also be the case that a light guide 15*b* or a plurality of light guides 15*b* at least partially only protrude(s) from the container casing 4 into the container inner volume 22.

The container interior 22 of a container 1 or a disposable bioreactor or a disposable bag 1*b* can, for example, assume values between approximately 15 ml and approximately 8000 liters, in particular between approximately 80 liters and approximately 5000 liters, and preferably between approximately 100 liters and approximately 1000 l.

It is particularly advantageous to use a disposable bioreactor or a disposable bag 1*b* if subsequent cleaning or sterilization, for example for cost reasons, is to be dispensed with. This can be the case if a particularly toxic medium 8 has been stored in the container interior 22 of a disposable bag, which can be disposed of together with the disposable bag more cheaply. It can also generally prove to be more cost-effective to use disposable bioreactors/disposable bags instead of reusable bioreactors in a multiplicity of processes taking place in a multiplicity of bioreactors. The purchase of a reusable bioreactor 1*a*, for example made of steel, and the cleaning or sterilization of such reusable bioreactors 1*a* often prove to be inefficient in terms of costs. In such cases, disposable bioreactors such as disposable bags 1*b* are preferred.

A preferred embodiment of a container 1 of a disposable bioreactor for single-use can comprise a container casing 4 or also other elements that substantially or at least partially formed of a so-called "soft plastic" or of a particularly flexible plastic, in particular a soft PVC and/or polyolefin, in particular polyethylene. Sections serving to stabilize the container structure, however, can be made of a harder material. Such elements and/or sections can be formed in part from a so-called "hard plastic" or from a more rigid or dimensionally stable plastic, in particular from a (meltable) thermoplastic or from a (non-meltable) thermoset, for example a synthetic resin. For example, a container access or a port 16, as well as hoses 18 and sections of a container bottom 1' could be formed from such a dimensionally stable plastic.

In particular, the plastic is substantially or at least partially sterilizable, e.g. using beta or gamma radiation. In general, the material used for the production of a container 1 or for the production of a bioreactor 1*a* can be sterilized by means of thermal sterilization, by means of steam sterilization, by means of hot air sterilization, by means of chemical and/or physical sterilization (e.g. beta or gamma radiation).

The embodiment of FIG. 3 further comprises a mixing device comprising a stirring element 3 with a stirring shaft 9 and rotor blades 5, a drive device 2 and a drive-side bearing 6 for mixing or stirring the medium 8 located in the container interior 22.

It can be the case, for example, that elements of the mixing device are formed at least partially from a metal and/or a stable plastic. For example, an element can also comprise a metal core, which is coated with as substantially inert or non-reactive plastic, such as Teflon. It can be the case, for example, that the disposable container/disposable bag 1*b* or the disposable bioreactor is substantially designed for single-use, wherein all elements are used only once. Alternatively, elements, for example a mixing device, can also be designed for reusable use. In particular, all elements and surfaces located at least inside the container interior 22 can be sterilized.

The container casing 4 of the disposable bag 1*b* is preferably transparent to electromagnetic radiation of at least one frequency range, in particular for at least part of the visible light. In this way, a medium 8 located inside the container interior 22 can be at least partially irradiated, for example from the outside A, by means of an artificial light source 15*d* or illuminant, preferably by means of a lamp and/or by means of a natural light source 15*d*, such as the sun.

It is expressly emphasized that a mixing device does not necessarily have to be part of a (single-use) bioreactor. An illuminant 15 and/or a light source 15*d* can also be attached or provided in another alternative manner in or on the disposable photo-bioreactor.

In an alternative embodiment, which is not explicitly shown here but is particularly preferred, a disposable bioreactor/disposable bag 1*b* can in particular comprise illuminant-receiving pockets 11. Essentially, such illuminant-receiving pockets 11 are configured similarly to previous embodiments, for example of FIGS. 1 and 2. Illuminant-receiving pockets 11 are preferably substantially designed to protrude onto the inside of the container I of the disposable bioreactor/disposable bag and to receive an illuminant 15, in particular a light-emitting rod 15*a*, from the outside A, so that the light-emitting rod 15*a*, which is only isolated from the medium 8 by the pocket wall 11*a*, can emit electromagnetic radiation 14 to the inside of the container I or to the medium 8 in the container interior 22. Such illuminant-receiving pockets 11 are preferably made of the same material as a large part of the container casing 4 and in particular are transparent.

Additionally or alternatively, sections of the inner surface of the container casing of a disposable bag 1*b* can also be provided, in particular over a large area, with an illuminant 15, for example with a light-emitting film or a light-emitting pad, and with light-emitting diodes (LEDs) or other light sources. Additionally or alternatively, light-emitting particles can also be provided in the container interior 22.

Additionally or alternatively, the stirring shaft 9 of the disposable bioreactor/disposable bag 1*b* can comprise a cavity, as well as a substantially transparent wall, so that an illuminant, such as a light-emitting rod 15*a*, can be received in the cavity and, through the transparent wall of the stirring shaft 9, light 14 can be emitted to the medium 8 or the container interior 22.

Hoses 18 and sensors 19 are also arranged on the disposable bag 1b of the present embodiment. The sensors 19 are each connected to lines 13. Such lines 13 can be, for example, power and/or data cables. Alternatively, a line 13 can also be a hose. This is not explicitly specified in this embodiment. Via the hoses 18, substances and/or a medium 8 can be supplied into the container interior 22 and/or drained or discharged from the container interior 22 to an outside A. Container accesses 16 and/or ports can be designed so that a hose can be arranged thereon. Alternatively or additionally, container accesses 16 and/or ports can be designed to receive an illuminant. For example, a port 16 may be a sealed access for a light-emitting rod 15a (not shown here). Or container accesses 16 and/or ports and/or container doors (not shown here) can, for example, be designed so that a sample of the medium 8 can be taken by hand. A disposable bioreactor/disposable bag 1b can also include an overpressure valve (not shown here) which, for example, can discharge or release a gas above a certain pressure threshold.

It should nevertheless be noted that other embodiments of disposable bioreactors do not necessarily have to have hoses 18, sensors 19 and lines 13.

Aspects and features mentioned as combinable features with respect to other embodiments but not explicitly with respect to the embodiment of FIG. 3 can also be explicitly combined with this embodiment, provided that they are not mutually exclusive with other aspects from the context.

Figure 4:
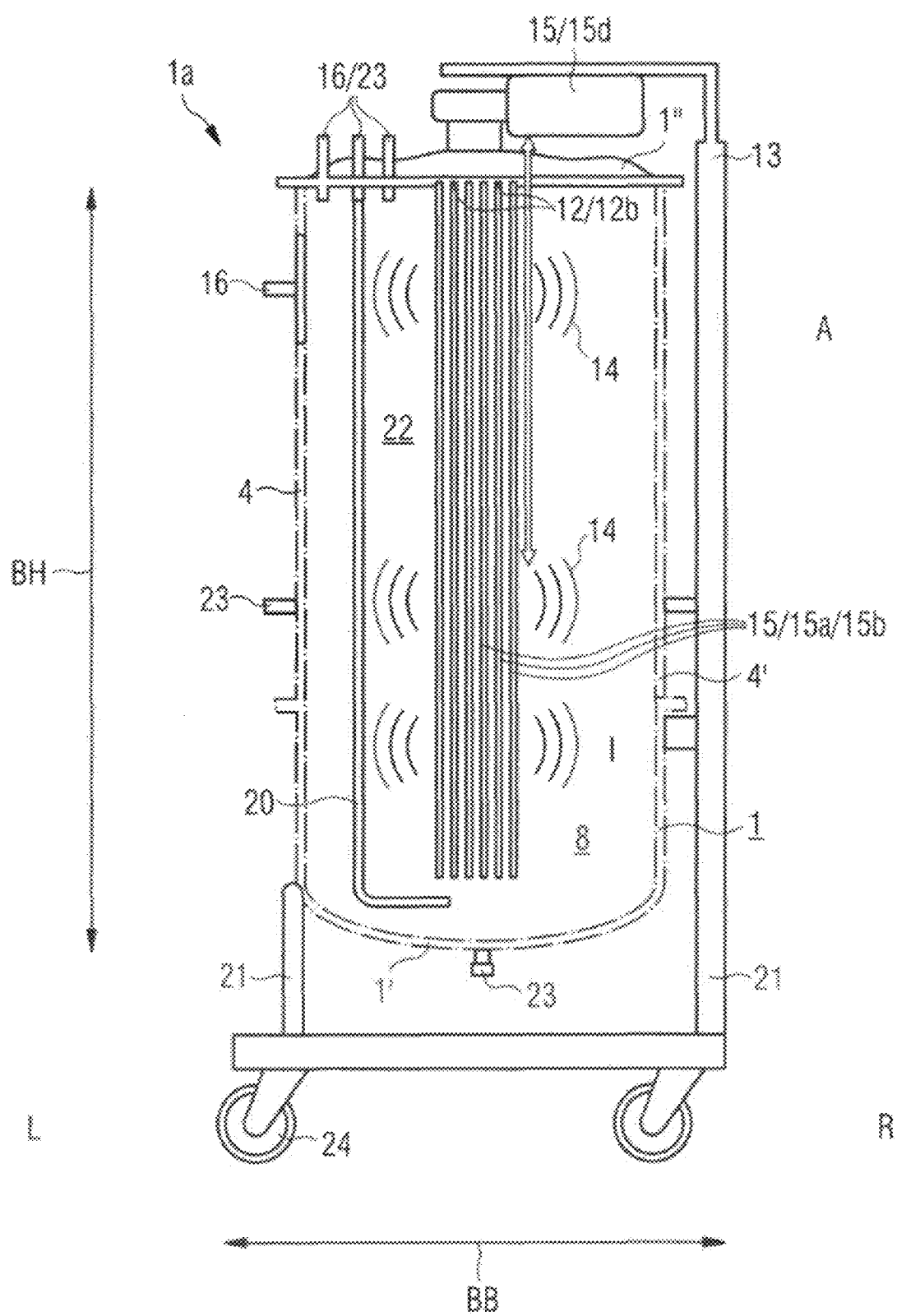
FIG. 4 is a schematic side view with a view into a tank or container of a bioreactor with several light guides as an exemplary embodiment.

FIG. 4 is an embodiment of a container 1 of a bioreactor 1a, in which a plurality of illuminants 15, for example in the form of light guides 15b, which can emit electromagnetic radiation during operation, are provided to irradiate a medium 8 located in the container interior 22. The plurality of illuminants 15 include in particular approximately 3 to approximately 1000, preferably approximately 10 to approximately 500, and particularly preferably approximately 20 to approximately 300 light guides 15b and/or light-emitting rods 15a. The bioreactor 1a or the container 1 can itself comprise the light guides 15b, or alternatively the light guides 15b can be arranged on the container 1 of the bioreactor 1a. For example, in an embodiment not explicitly shown here, it may be possible that all of the light guides 15b are received by a single illuminant-receiving pocket 11 or that each individual light guide 15b is received by an illuminant-receiving pocket 11 and are isolated from the medium 8 by the pocket wall 11a. Alternatively, the light guides 15b can also be in direct contact with the medium 8, in particular if the light guides 15b are designed to be sterilizable. Instead of light guides 15b or some light guides 15b, however, the illuminants shown can alternatively or additionally also be light-emitting rods 15a.

The illuminants 15 are attached to the container lid 1" or to the container ceiling. The sections of the illuminants 15 which are substantially arranged on the inside of the container I are connected to elements on the outside A, for example to light sources 15d, such as a laser, via one or more illuminant openings 12 or illuminant openings in the container lid 12b. A light source 15d can in turn be connected by means of a line 13, for example a power cable, by which the light source 15d is supplied with energy. In order to ensure a particularly large or efficient irradiation, the illuminants in the embodiment shown substantially extend from the container lid 1" substantially to or almost to the container bottom 1'. The light guides 15b and/or light-emitting rods 15a can preferably extend over a length between approximately 0.1 and 5 m, in particular between approximately 0.3 m and approximately 3 m, and particularly preferably between approximately 1 m and 1.8 m. In the event that there are light guides 15b and these are arranged or bent and/or wound in any shape, a light guide 15b can have a length of about 0.1 m to approximately 50 m, in particular of approximately 2 m to approximately 30 m, and preferably from approximately 3 m to approximately 15 m.

The container casing 4 of the container 1 of FIG. 4 can be made substantially non-transparent and preferably made of a metal, for example steel. Alternatively or additionally, the container casing 4 of the embodiment shown can be at least partially or completely transparent, in particular made of a glass and/or a transparent plastic. For example, the container casing 4 of the container 1 can also comprise a transparent window through which electromagnetic radiation from the outside A can pass to the container inside I, for example emitted from an external light source.

The container 1 of the bioreactor 1a according to FIG. 4 is supported or mounted and/or hung and/or held by a frame 21. The frame 21 has rollers 24, by means of which the bioreactor 1a can be pushed and/or pulled to a destination. The container 1 of the bioreactor 1a further comprises container accesses 16 or ports through which the medium 8 is accessible for the addition or removal of a substance. By means of drains 23, which can also be used as inlets, a medium 8 can be at least partially drained from a container interior 22, or a container interior 22 can be at least partially filled with a medium 8. In particular, a hose can be attached to an outlet 23.

Aspects and features mentioned as combinable features with respect to other embodiments but not explicitly with respect to the embodiment of FIG. 4 can also be explicitly combined with this embodiment, provided that they are not mutually exclusive with other aspects from the context.

Figure 5:
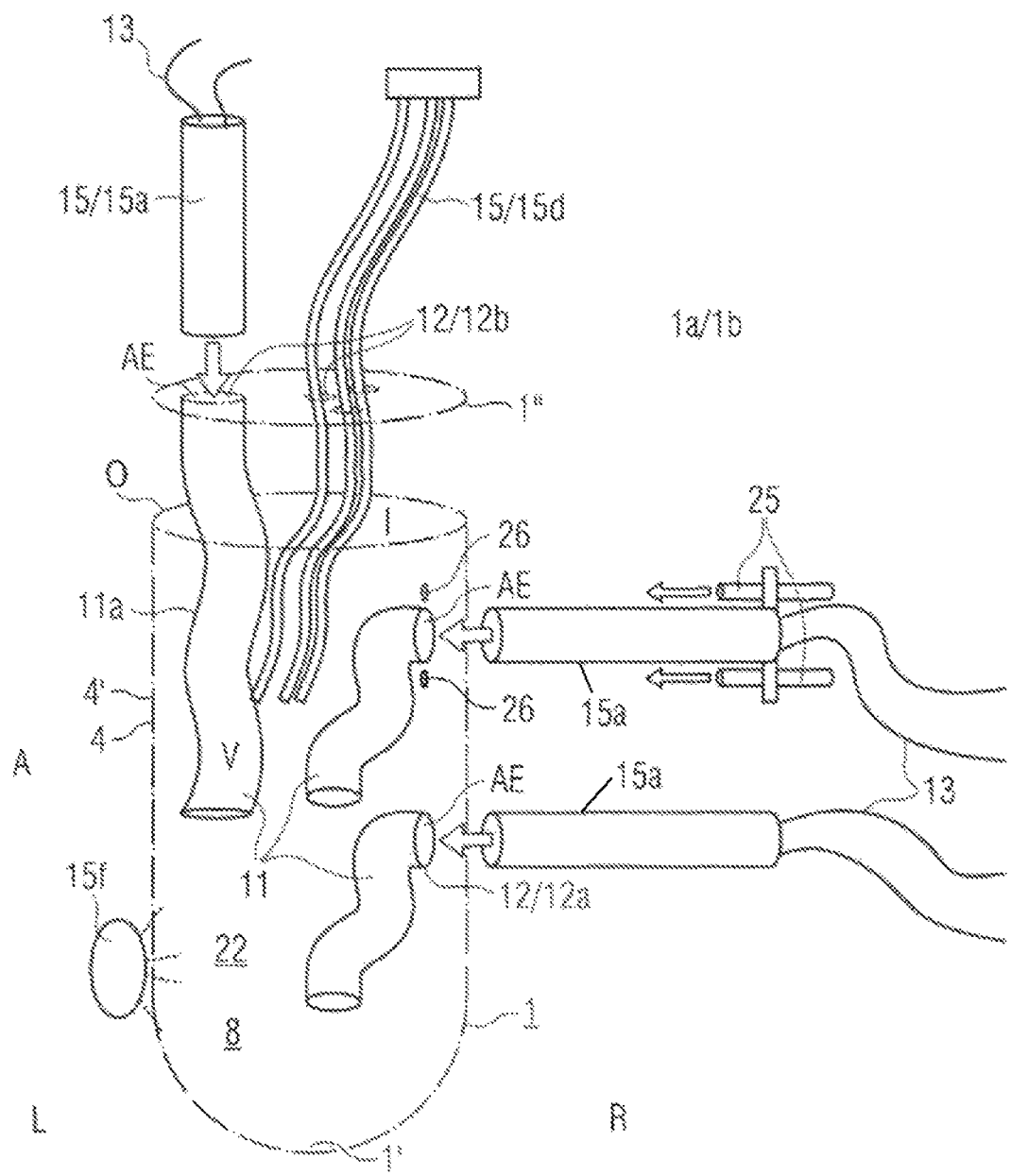
FIG. 5 is a schematic exploded view with a view into a tank or container of a bioreactor with a container lid, illuminant-receiving pockets on the container casing and the container lid, with one or more attachable light guides, illuminants and/or external illumination according to a further embodiment.

In the embodiment of a container 1 according to the exploded view in FIG. 5, there are a large number of different illuminants 15. The container 1 can in particular be a disposable container. The container 1 can be formed from a substantially stable or rigid or solid material, for example the container 1 can be at least partially made of a metal, in particular steel and/or at least partially made of a solid plastic, in particular a transparent plastic and/or be made of glass. In particular, a container 1 for single-use can be a single-use or disposable bag.

An external illuminant 15f is initially indicated on the left-hand side L. The external illuminant 15f can be a lamp or other light source 15d, which is arranged on the outside A in such a way that a light 14 emitted by the lamp can propagate into the container interior through a substantially transparent section of the container casing 4. A medium 8 can thus also be irradiated from the outside.

The container 1 further comprises a container casing 4, as well as a container lid 1", which can be arranged on the upper edge O of the container 1. The container interior 22 or the container inside I can be isolated from the outside A permanently or over a longer period of time, or can be open or opened over a period of time, for example, by opening the container lid 1". The container casing 4 and the container lid 1" each comprise illuminant openings 12, namely two illuminant openings in the container wall 12a, and one illuminant opening in the container lid 12b. At the illuminant openings in the container wall 12a and the illuminant opening in the container lid 12b, illuminant-receiving pockets 11 can be arranged. In particular, the container interior 22 and the outside A are separated by a sealed connection between the illuminant opening 12 and illuminant-receiving pockets 11, so that no medium 8 located in the container interior 22 can unintentionally escape to the outside. This also presupposes that the illuminant-receiving pockets 11 each comprise a sealed or dense pocket wall 11a.

An illuminant 15, in particular a light-emitting rod 15a, can be pushed or moved and/or arranged or stored in an illuminant-receiving pocket 11 or in a pocket inner volume V of an illuminant-receiving pocket 11. In the embodiment of FIG. 5, there are two light-emitting rods 15a each on the right side R still on the outside A. Both light-emitting rods 15a can be moved or pushed, by movement or displacement in the direction of the container casing 4, which is shown in the figure, substantially horizontally through the container wall openings 12a or the openings in the container casing 4 and the reception entrances AE of the illuminant-receiving pockets 11, into the respective pocket inner volume V. The illuminant-receiving pockets 11, which are arranged on the right-hand side R of the container casing 4 in FIG. 5, hang down from the container casing 4 in the container interior 22 in the direction of the container bottom 1'. They are in an unfilled condition. As soon as the light-emitting rods 15a are at least partially pushed into the illuminant-receiving pockets 11, the illuminant-receiving pockets 11 are in an at least partially filled state.

In the embodiment according to FIG. 5, there is also a light-emitting rod 15a above the container lid 1" on the outside A. The light-emitting rod 15a can be moved or pushed, by movement or displacement in the direction of the container lid 1", which is shown in the figure, through the container lid opening 12b or the openings in the container lid 1" and the reception entrances AE of the illuminant-receiving pocket 11, into the pocket internal volume V.

In order to secure a light-emitting rod 15a to a container 1, the container 1 can comprise fastening means 26, for example a thread and/or a pressure connection and/or a clamp. A light-emitting rod 15a or another illuminant 15 can then be fixed or secured or attached to the container 1 by means of a suitable fastening means, for example by means of a screw and/or a groove and/or a hook.

In operation, in particular if the illuminants 15 are supplied with current, in particular in each case via lines 13 or power cables, an illuminant 15 can then emit electromagnetic radiation.

In the present embodiment, the container lid 1" also comprises an illuminant opening in the container lid 12b, through which light guides 15a can be guided into the container interior 22 from the outside. The light guides 15a can be isolated from the medium 8 by one or more illuminant-receiving pockets 11 or be in direct contact with the medium 8.

Aspects and features mentioned as combinable features with respect to other embodiments but not explicitly with respect to the embodiment of FIG. 5 can also be explicitly combined with this embodiment, provided that they are not mutually exclusive with other aspects from the context.

Figure 6A:
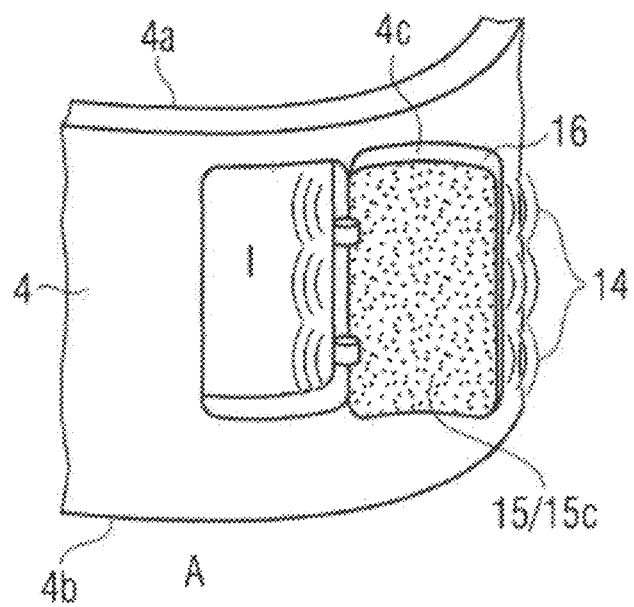
FIG. 6a is a perspective side view of a section of a container casing with a door according to a further embodiment.

With regard to the embodiment according to FIG. 6a, a section of a container casing 4 with a container door 16 is shown. The container casing 4 comprises a container casing inner surface 4a, which is an inner surface of the container casing 4 facing the container interior. In addition, the container casing 4 comprises an container casing outer surface 4b, which is an outer surface of the container casing 4 facing an outside A. The container door 16 is an access to the container interior 22 or to the container inside I from the outside A. The container door 16 comprises a door wall 4c, the inner surface of which, when closed, is preferably flush with the container casing inner surface 4a. In the closed state, the outer surface of the door wall 4c is preferably flush with the container casing outer surface 4b.

In particular, the inside of the door wall 4c comprises an illuminant 15, which can be a light-emitting film 15c, for example. The light-emitting film 15c can output or emit electromagnetic radiation 14 to the container interior 22 and a medium 8 located therein, particularly in the closed state.

Figure 6B:
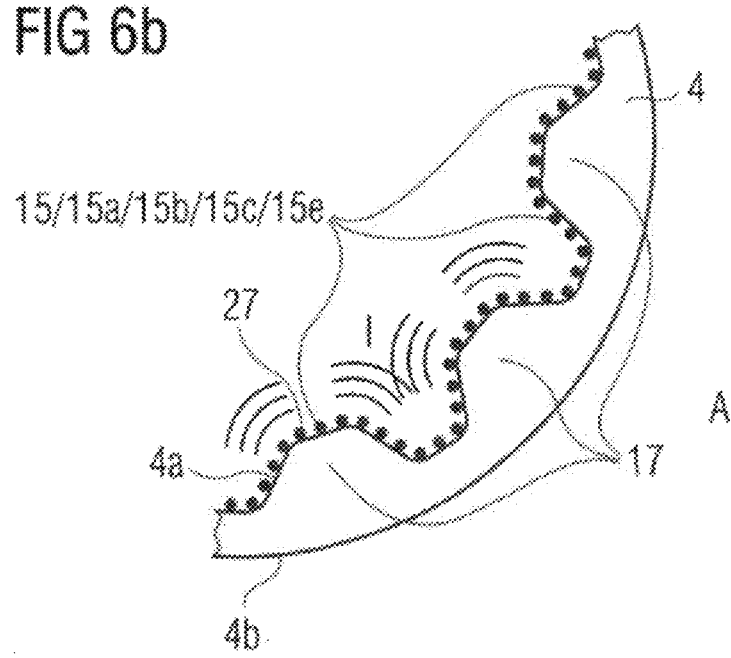
FIG. 6b is a top or bottom view of a section of a container casing cross section with a container inner wall structure and illuminants according to a further embodiment.

With regard to the embodiment of FIG. 6b, a view of a detail or section of a container casing 4 is shown from above. A container casing 4 comprises a container casing outer surface 4b, as well as a structured, in particular corrugated container casing inner surface 4a or a container inner wall structure 17 which substantially faces the inside of the container I. The container inner wall structure 17 can, as shown in the present embodiment, comprise projections or recesses and indentations. The structured or corrugated or wound configuration of the container casing inner surface 4a makes it possible to provide a larger surface on which illuminants 15 or light sources can be arranged and from which a light 14 can be emitted into the interior 22 of the container.

Light-emitting rods 15a, light guides 15b or light-emitting fibers and/or light-emitting films 15c, light sources 15d, in particular light-emitting diodes 15e, can be arranged or attached or fixed on the container casing inner surface 4a, so that they can emit electromagnetic radiation 14 to the container inner volume 22 during operation.

The container inner wall structure 17 creates a surface 27 that is enlarged compared to or with respect to an unstructured container casing inner surface 4a, on which substantially more illuminants 15 can be arranged than on an unstructured container casing inner surface 4a. A container casing inner surface 4a can, for example, also be structured such that a preferred flow profile of a medium 8 can be generated, in particular if a container 1 has a mixing device that can mix or stir the medium 8.

Aspects and features mentioned as combinable features with respect to other embodiments but not explicitly with respect to the embodiment of FIGS. 6a and 6b can also be explicitly combined with this embodiment, provided that they are not mutually exclusive with other aspects from the context.

Figure 7:
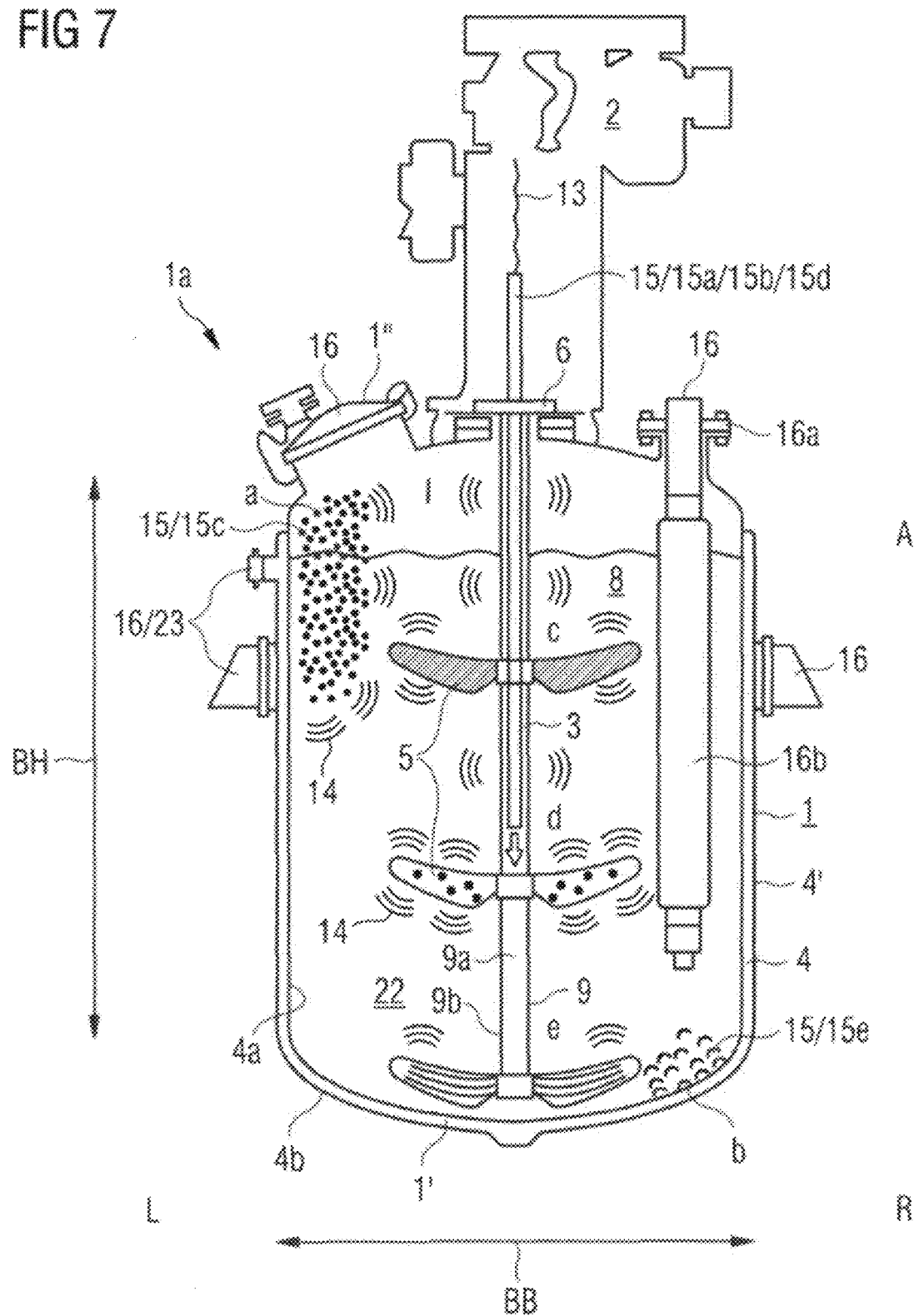
FIG. 7 is a cross-sectional view of a container of a bioreactor with a mixing device and various illuminants according to a further embodiment.

FIG. 7 shows a further embodiment of a container 1 of a bioreactor 1a comprising various illuminants 15 and/or light sources. The container 1 of the bioreactor 1a comprises a container casing 4 with a container casing inner surface 4a and a container casing outer surface 4b. The container casing inner surface 4a can comprise areas or sections on which light-emitting elements or illuminants can be arranged. Such light-emitting container inner wall sections are identified, for example, by the reference symbols a and b in the present figure. For example, a light-emitting film 15c can be arranged on a light-emitting container inner wall section a. For example, light-emitting diodes 15e can be arranged on another light-emitting container inner wall section b. Such illuminants 15 can be supplied with the energy required for operation via a battery and/or via a power supply using one or more power cables (not shown here). For example, there may be a cavity between the inner surface 4a of the container casing and the outer surface 4b of the container casing, through which cables and lines can be led to the corresponding illuminants 15 (not shown here). The illuminants 15 on the inner surface 4a of the container casing can be isolated from the medium 8 by means of a film, for example. The illuminants 15 on the inner surface 4a of the container casing can also be reversibly attached and removed. For example, the inner surface 4a of the container casing can comprise plug-in connections to which illuminants 15, for example light-emitting diodes 15e, can be attached.

The present embodiment of a container 1 of a bioreactor 1a also comprises a mixing device with rotor blades 5 or stirring extensions. Light-emitting elements or illuminants 15 can preferably be arranged on the surfaces of the rotor blades 5. Light-emitting rotor blade sections are indicated in particular by the reference numerals c, d and e. On a preferred light-emitting rotor blade section c it is indicated that a light-emitting film 15c is arranged thereon. On a further preferred light-emitting rotor blade section d it is indicated that a plurality of light-emitting diodes 15e are arranged thereon. On another preferred light-emitting rotor blade section e it is indicated that a plurality of light guides 15b are arranged thereon in parallel to one another. One or more rotor blades can also be designed only according to the rotor blade section c or d or e.

In particular, the present embodiment of a container 1 of a bioreactor 1a comprises a stirrer shaft 9, which substantially extends from the container ceiling to the container bottom 1'. The stirrer shaft 9 comprises a stirrer shaft cavity 9a and an at least partially transparent stirrer shaft wall 9b. As indicated in FIG. 7, a light-emitting rod 15a and/or a light guide 15b and/or a (substantially rod-shaped) light source 15d can be received by the stirring shaft cavity 9a, so that the light-emitting rod 15a in operation can emit electromagnetic radiation 14 to the container interior 22, which is preferably at least partially filled with a medium 8.

Furthermore, the container 1 of the bioreactor 1a comprises a container access 16 with an access tube 16b and a valve 16a arranged substantially on the right side R on the upper container ceiling. The container access 16 allows substances from the outside A, for example gases and/or liquids, to be fed into the container interior 22. In addition, the container 1 of the bioreactor 1a also substantially has an access 16 with a container lid 1″ or container door or container flap on the left side L on the container ceiling, which access can be opened and closed. With such an opened container lid 1″, for example, a granulate or another solid can be supplied to the medium 8 on the inside I of the container from the outside A. The container 1 of the bioreactor 1a also comprises several other container accesses 16 on its container casing 4, through which substances can be supplied to or removed from the container inner volume 22.

Aspects and features mentioned as combinable features with respect to other embodiments but not explicitly with respect to the embodiment of FIG. 7 can also be explicitly combined with this embodiment, provided that they are not mutually exclusive with other aspects from the context.

FIG. 8a is the frontal view of a bioreactor 1a with a steel casing, which comprises a disposable bag 1b corresponding to or at least similar to the design of the disposable bag 1a of FIG. 3 in its inner volume. FIG. 8b is the frontal view of a partially opened bioreactor 1a with a steel casing and opened container door 16, which contains a disposable bag 1b visible in its inner volume according to the embodiment of FIG. 8a.

FIG. 8c is the frontal view of a disposable bag 1a corresponding to or at least similar to the embodiment of the disposable bag 1a of FIG. 3, which can be received by the bioreactor 1a with a steel casing according to the embodiment of FIGS. 8a and b.

Figure 9A:
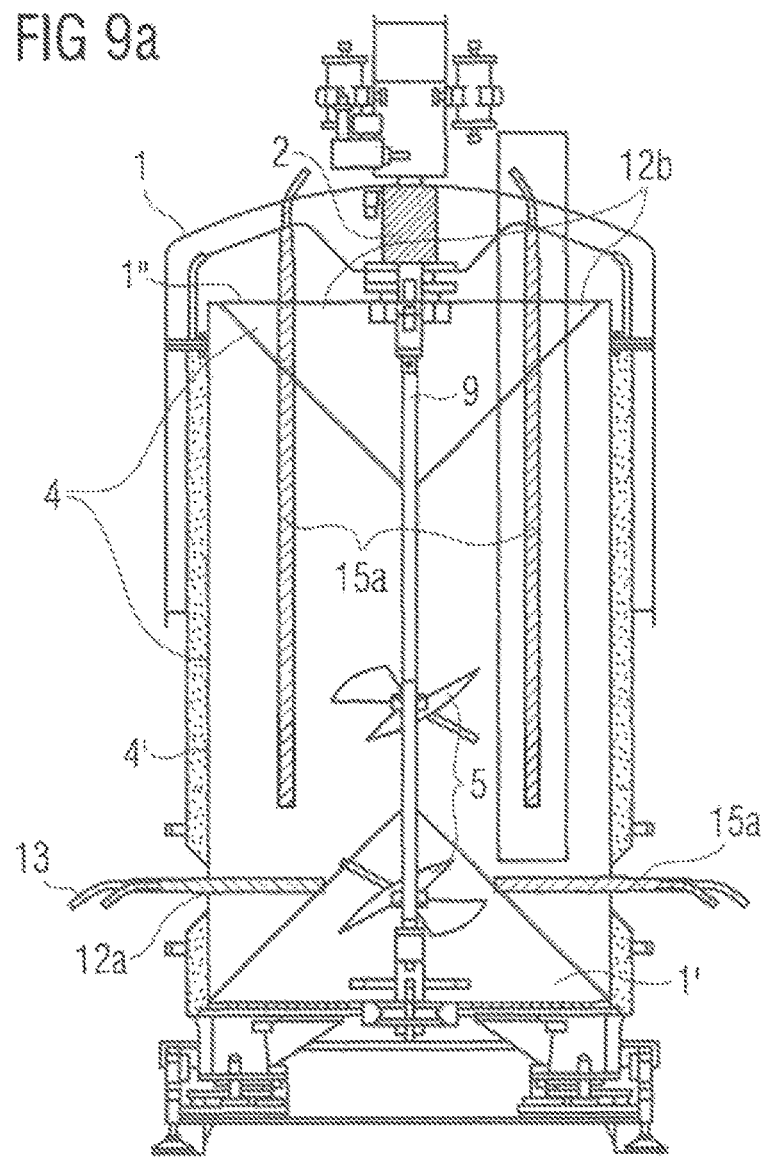
FIG. 9a is a schematic side view with a view into a disposable container of a bioreactor with a mixing device and light sticks according to a further embodiment.

FIG. 9a is a frontal view looking into a container 1 of a bioreactor according to an embodiment. In this embodiment, light-emitting rods 15a are embedded in the circumferential wall of the container casing 4' and in the ceiling of the container casing 4. The light-emitting rods 15a are arranged through illuminant openings 12a in the container wall or in the container casing 4 on the inside of the container 1, and in particular inside the illuminant-receiving pockets 11. The light-emitting rods 15a are also arranged through illuminant openings 12b in the container ceiling on the inside of the container 1, and in particular within illuminant-receiving pockets 11.

In other words, according to one aspect, the container 1 comprises at least one illuminant opening 12b on a section of a container ceiling, and at least one illuminant opening 12a on a section of a container wall or container casing 4. An illuminant-receiving pocket 11 is preferably arranged on an illuminant opening 12a, 12b.

Alternatively, it is also possible for the light-emitting rods 15a not to be arranged inside the illuminant-receiving pockets 11, but to be in direct contact with the interior or with the medium in the interior. This would be the case in particular if the light-emitting rods 15a are permanently arranged on the container 1 or are not removed from the container when it is filled with a medium.

Figure 9B:
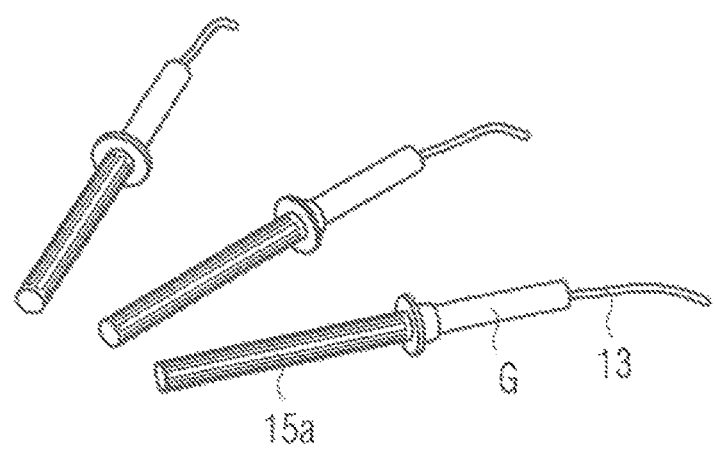
FIG. 9b shows three light sticks according to a further embodiment.

FIG. 9b is a view of three light-emitting rods 15a according to an embodiment. The light-emitting rods 15a each include a handle G for handling. The handle G can also be useful in that the light-emitting rod 15a does not have to be touched directly at a possibly hot and/or at a sensitive point. The handle G can also serve to remove the light-emitting rod 15a from the container 1 when it is arranged on and/or in the container 1. The light-emitting rod 15a is supplied with current by means of a line 13 or by means of a cable.

FIG. 10a is a frontal view looking into a container 1 of a bioreactor according to an embodiment. In this embodiment, illuminants 15, in particular light-emitting rods 15a with light-emitting fibers/light guides 15b and/or rods with light-emitting fibers/light guides 15b, are embedded in the peripheral wall of the container casing 4' and in the ceiling of the container casing 4. The rods and/or the light-emitting rods 15a with the light-emitting fibers/light guides 15b are arranged in the container wall or in the container casing 4 on the inside of the container 1 through lamp openings 12a. They can be in direct contact with the inside and/or with the medium on the inside, or they can be arranged within illuminant-receiving pockets 11. The light-emitting rods 15a are also arranged on the inside of the container 1 through lamp openings 12b in the container ceiling.

In other words, an illuminant 15 can comprise a light-emitting rod 15a, on which light-emitting fibers 15b are arranged. An illuminant 15 can generally comprise a rod on which light-emitting fibers 15b are arranged. An illuminant 15 can in particular comprise a hollow, transparent rod with an interior through which light-emitting fibers 15b are guided/directed, which escape from the interior at various openings in the hollow, transparent rod. This embodiment has the advantage that the area of the illuminant 15 is particularly large. In other words, a particularly large area is generated, which can emit light in particular to a medium surrounding the illuminant 15. In this case, the hollow rod can also be regarded as a light-emitting rod 15a, although it does not itself emit light, but the light-emitting fibers 15b do emit light. The arrangement of the rods or the light-emitting rods 15b through illuminant openings 12a, 12b in the container casing 4 and in the container ceiling is particularly advantageous, since in this case a particularly large light-emitting area is generated. In particular, the light-emitting fibers 15b are designed to be flexible, so that they can move partially along with a moving medium.

A plurality of light-emitting fibers 15b are likewise arranged in a bristle-like manner on the stirring shaft 9. In particular, an attachment device 29 for a plurality of light guides or light-emitting fibers 15b is arranged on the stirring shaft. A hollow transparent stirring shaft 9 is particularly preferred, within the cavity of which an illuminant 15, for example a light-emitting rod 15a and/or a light-emitting fiber 15b, is arranged.

The light-emitting fibers 15b can be in direct physical contact with a medium on the inside of the container 1 or can be arranged within one or more illuminant-receiving pockets 11.

FIG. 10b is a perspective view of an attachment device 29 for a plurality of light guides or light-emitting fibers 15b according to one embodiment. The attachment device 29 comprises a ring 29', for example a metal and/or plastic ring. In particular, the ring is made transparent. Circularly light-emitting fibers 15b are arranged on the outer circumference of the ring 29', which protrude away from the ring 29' or outwards. The light-emitting fibers 15b are arranged circularly next to one another in a row of a plurality of light-emitting fibers 15b. In the embodiment shown, twelve rows of three fibers 15b lying one above the other are arranged in a circular manner. Alternatively, a different number can also be selected.

FIG. 10c is a perspective view of three rods and/or light-emitting rods 15a with light-emitting fibers/light guides 15b. The rods each comprise a handle G and a cable or line 13 for power supply.

In general, illuminants 15 can be arranged in particular flat on the inside of the wall of the bioreactor 1a or steel tanks, so that the medium 8 in the disposable bag 1b can be illuminated through the container cover 4. Furthermore, an illuminant 15, in particular a fiber or a light guide 15b, can be arranged, in particular wound, around the stirring shaft at least partially or in sections.

The bioreactor 1a comprises a computing unit 28, which is designed to control and/or regulate, for example, a temperature, a pump flow, a pressure and/or an illuminance by the illuminants 15.

Containers 1, 1b, mixing systems and pellet tanks substantially serve to accommodate, store and mix biological media 8, e.g. fluids and/or solids and/or gases. Biological media can be provided in containers 1, 1b, e.g. bags 1b, in particular in plastic bags, which can have a volume of several hundred liters. The biological media 8 can preferably be introduced into such a bag 1b in the bioreactor 1a, in which they can be stored, temperature-controlled and/or mixed and irradiated. Different photoreactive processes or reactions within the biological medium 8 can be triggered in such a container 1 of the (photo) bioreactor.

A container 1, 1b can be a component of a bioreactor 1a and/or a fermenter. For example, a container can also be a component of a food tank or food barrel or a silo or a store. A container 1, 1b can also be part of a laboratory device, in particular a chemical laboratory device. For example, a container can be a column for column chromatography.

An illuminant receiving pocket 11 can, for example, preferably be made of a soft plastic as a flexible and/or stretchable and/or foldable and/or movable pocket (in the sense of a bag or a pocket). However, an illuminant-receiving pocket 11 can also be a hollow and substantially transparent tube made of glass and/or a hard plastic or resin, which can be designed and sterilized for multiple use.

Liquids, gases, suspensions, dispersions, buffers and/or cell culture broths are regarded as the medium 8 or media 8 in the context of the present invention. Media 8 can also include solids, such as powders, granules, pressed pellets, particles, grains, and mixtures thereof. A medium 8 can accordingly comprise different constituents with the same or different aggregate state, for example an emulsion or a dispersion.

A photoreactive or photosensitive or light-sensitive medium can in particular comprise biochemical materials, in particular biological materials. For example, such a medium can include plants, in particular algae and microalgae and/or bacteria, in particular purple bacteria and/or cyanobacteria, fungi, plant and/or animal cells, for example moss cells, eukaryotes and/or prokaryotes, and corresponding mixtures thereof. Whole plants, such as duckweed and/or tissue components, can also be contained in the medium, for example in a suspension. Irradiation can trigger a biochemical process, especially photosynthesis in cells. The media are preferably substances that undergo biological processes. In particular, they are heterotrophic, phototrophic and/or mixotrophic processes.

The term photoreactive or photosensitive or light-sensitive substance generally includes molecules and atoms, as well as larger building blocks made of molecules and/or atoms, for example macromolecules or quantum dots, which react to irradiation with light or electromagnetic waves with a chemical and/or biological and/or biochemical and/or physical reaction. In particular, media, such as the aforementioned, comprise proteins that undergo photochemical processes due to the irradiation of light. For example, plants, algae and cyanobacteria contain so-called complexes, i.e. proteins in lipid/cell membranes, which are responsible for the turnover of photosynthesis.

In general, photoreactive or photosensitive or light-sensitive substances can be, for example, photosensitive proteins. Azobenzene, hydrogen peroxide, fluorescent and/or phosphorizing substances, quantum dots, graphenes or other substances can also be involved in photochemical reactions.

The terms photoreactive substance, photosensitive substance and light-sensitive substance used here have substantially the same meaning and mean, for example, the substances mentioned above, which can react by means of light irradiation or exposure to light. In particular, what is meant here are such photoreactive or photosensitive or light-sensitive substances that each undergo a photochemical, in particular photo-biochemical reaction. What can be meant here are such photoreactive or photosensitive or light-sensitive substances that carry out photochemical processes such as photosynthesis and thereby reversibly pass through different stages or states. However, what can also be meant are such substances that are educts, which are converted into products by means of light irradiation. The photochemical reaction can take place in stages of different photochemical reactions or in stages of different reaction at least comprising a photochemical reaction. The term "reaction" can also include physical and/or biological reactions or phenomena. For example, electromagnetic (heat) radiation can cause the pressure and/or inside a container to rise, which in turn can influence the photochemical reaction.

A photochemical reaction is typically understood to mean those chemical reactions that are initiated, triggered or prompted under the action or absorption or irradiation of light or electromagnetic radiation. This usually requires absorption of light or electromagnetic radiation by a molecule or atom that takes part in the photochemical reaction. This means that the wavelength or frequency of the light used must be matched to the absorption behavior of the molecule. This substantially concerns an immediate or direct photochemical reaction. However, there are also photochemical reactions or photoreactions in which a so-called photosensitizer is first excited by means of light and this photosensitizer then transfers energy to molecules that take part in a chemical reaction, for example in an endothermic reaction. In this way, a chemical reaction can be triggered indirectly. A process, for example a chemical process, can comprise one or more reactions, in particular a photochemical reaction. If a medium 8 undergoes a process, it can be said that the medium 8 is being processed, that is to say it is converted from an initial state to an end state by one or more reactions. The medium 8 may initially comprise or be one or more educts, and at the end of the process the medium 8 may comprise or be one or more products.

For example, such a photochemical reaction can include one or more of: cleavage or bond homolysis or fragmentation of molecules, photoisomerizations, electrocyclic reactions, rearrangements, light-induced chain reactions, photo-Fries shifts, isomerizations, for example cis-trans isorizations, biological photoreactions and photophysical processes, especially chlorination, electrocyclic reactions, nitrosylation, oxychlorination, oxidation, catalyzed oxidation, sensitized oxidation, cationic polymerization, radical polymerization, sulfochlorination, sulfoxidation. In such reactions, changes in electronic states in molecules and atoms are often caused or triggered by the absorption of light or photons or electromagnetic radiation. Particularly noteworthy is, for example, photosynthesis, especially anoxygenic photosynthesis or oxygenic photosynthesis of biological substances. Special proteins are involved in photosynthesis, which are present, for example, in plant or bacterial substances or can be obtained from plant or bacterial sources. Specifically, for example, a medium can comprise one or more types of algae that absorb light to carry out photosynthesis.

The absorption of light or electromagnetic radiation substantially leads, even in photo-biochemical processes, to energetically and/or electronically excited states that can undergo (bio)chemical reactions due to the excitation energy. Chemical conversions can compete with photophysical deactivation processes such as photoemission from the excited singlet state (fluorescence) or from the triplet state (phosphorescence) and radiation less deactivation.

The concept of the visible wavelength range relates to the wavelengths of light which are substantially visible to a person, in particular between approximately 380 nm to approximately 780 nm. The concept of the invisible wavelength range relates to the wavelengths of light which are substantially invisible to a person, for example, wavelengths shorter than about 380 nm or longer than about 780 nm. The term light used here is not limited to the visible spectral range, but rather relates to electromagnetic radiation in general. A "transparent wall" can be translucent or transparent to at least part of the light of these wavelengths or these frequency ranges. The term "translucent wall" is often limited to the translucency of light of an at least partially visible spectrum. A "transparent wall", on the other hand, can be transparent to visible and/or invisible light.

An illuminant 15 can be a light source 15*d*, for example. An illuminant 15 can also be a light guide 15*b* or optical waveguide or an optical fiber, which only transports the light emitted by a light source 15*d* to a specific location, where it is used e.g. to irradiate a medium 8. In other words, the term "illuminant 15" used here can be a light-generating source 15*d* or a light source 15*d*, or alternatively it can be a light-transporting and in particular a light-emitting means, such as an optical fiber or a light guide 15*b*. The terms illuminant 15 and light source 15*d* used here only differ in that a term of the illuminant 15 used in this description represents a generic term which, however, encompasses the term light source 15*d*. The illuminant 15 is substantially characterized in that it emits light, in particular in the direct vicinity of the medium 8, but does not necessarily also generate the light itself. In general, illuminants 15 and light sources 15*d* are also referred to below as light-emitting elements.

Light sources 15*d*, in particular light sources for the so-called "photosynthetic active radiation", which are used in photochemistry, in particular in photo-biochemistry and/or for photosynthesis, can generally be divided into continuous and discontinuous emitters. The power required also plays a role in the selection of the light source 15*d*. In particular, light sources 15*d* are used which have a power of approximately 0.1 watts to approximately 10000 watts, in particular of approximately 5 watts to approximately 6000 watts, and preferably of approximately 1500 watts to approximately 5000 watts. Light sources 15*d* are also used which have a power of approximately 0.1 watt/m2 to approximately 10000 watt/m2, in particular of approximately 5 watt/m2 to approximately 6000 watt/m2, and preferably of approximately 1500 watt/m2 to approximately 5000 watt/m2. Sunlight can have a power of about 1500 to about 2000 watt/m2. In principle, the illumination of a bioreactor should have the same or preferably a higher power, especially for cultivation in the high cell density range.

Continuous light sources 15*d* can emit light that can have a wide wavelength range. Black emitters are often used. So-called black emitters can be, for example, the sun or incandescent lamps. The frequency spectra of black emitters are characterized by a very wide or broad spectral distribution. The spectral distribution can range from the infrared, in particular the far infrared (thermal radiation) range, the visible frequency spectrum to the (near) UV range. However, the UV components of such black emitters can be low, which is why other light sources are also used for photosynthesis or chemistry, which also cover a frequency range that at least partially covers or comprises a UV region. For example, gas discharge lamps based on hydrogen/deuterium or noble gases are suitable as continuous emitters in the UV range.

At any position within the container, a luminous flux can have a value of, for example, from about 10 lumens to about 10,000 lumens, in particular from about 100 lumens to about 7000 lumens, and preferably from about 500 lumens to about 6000 lumens. A "light quantity" or the "quantity of light", in particular the sum of light in relation to the PAR ("photosynthetic active radiation"), evaluates the radiation of 400-700 nm, the spectral range that is actively used by plants, especially for photosynthesis. The measurement unit of this light sum of the PAR is $\mu mol/(s \cdot m^2)$. For example, a sum of light of about 40 to about 200 μmol/m2s can be emitted.

Illumination can take place, for example, by means of pulsed illumination, for example stroboscopically. This creates a flashing light effect. The flashing light effect ensures that photosynthesis in the cell is improved if the cells are only exposed to short flashes of light instead of continuous light. The flashing light effect can be achieved by appropriate mixing in the photobioreactor, because light only has a low depth of penetration into the culture and by the suitable illumination duration, which can be achieved by appropriate mixing (among others, with the help of baffles or illuminated baffles in SU bioreactor for standard drive), the cells can circulate between light and dark zones in the bioreactor and thus grow faster due to the flashing light effect. In particular, a disposable container with a stirring device can be equipped with light-emitting surfaces in such a way that the flashing light effect can be achieved by suitable mixing and thereby suitable illumination times for the cells and/or bacteria and/or algae. In this regard, all of the above-mentioned forms for producing light-emitting surfaces can be combined in particular in a disposable container/biorector.

A light source 15d may generally comprise a laser, a diode, a globar, a Nernst lamp, an arc lamp, an incandescent lamp, a phosphor, a light emitting diode 15e (LED) and/or other light emitting means. Further, sunlight can be captured and/or bundled and directed into the container interior. Thus, the sun can also serve as a light source.

Light sources 15d can preferably emit electromagnetic radiation that is at least partially in a frequency range visible to humans. Additionally or alternatively, light sources 15d can also emit light of a wavelength or frequency that is at least partially or completely outside the frequency range visible to humans. For example, light sources 15d can emit light that has a frequency in the UV range and/or in the infrared range. In particular, light sources 15d can emit light of a wide frequency spectrum. Alternatively, a light source 15d, for example a laser, can also emit light that is very narrow-band in terms of frequency.

A bioreactor according to one of the aspects mentioned can further comprise an active and/or passive temperature control system, which can, for example, dissipate and/or supply heat. In particular, this can serve to prevent overheating of living organisms in the medium due to strong radiation.

REFERENCE NUMERAL LIST 1 container
1' container bottom
1" container lid/container ceiling
1a bioreactor
1b single-use or disposable bag
2 drive device
3 stirring element
4 container casing
4' peripheral wall of the container casing
4a container casing inner surface
4b container casing outer surface
4c container door wall
5 stirring extension/rotor blade
6 drive-side bearing
7 counter bearing
8 medium/biological medium
9 stirring shaft
9a stirring shaft cavity
9b stirring shaft wall
10 axial three-phase machine
11 illuminant-receiving pocket
11a illuminant-receiving pocket wall/pocket wall
12 illuminant opening
12a illuminant opening in the container wall
12b illuminant opening in the container lid/container ceiling
13 line
14 electromagnetic radiation/light
15 illuminant/light-emitting medium
15a light-emitting rod
15b light-emitting fiber/light guide
15c light-emitting film
15d light source
15e light-emitting diode
15f illuminant or light source attached to container casing from the outside
16 container access/port/container door
16a valve
16b access tube
17 container inner wall structure
18 hose
19 sensor
20 tube
21 frame/scaffold
22 container interior/container inner volume
23 inlet/outlet
24 rollers
25 fixation means to illuminant
26 fixation means to container
27 surface enlarged with respect to an unstructured container casing inner surface
28 electronically controlling/regulating computing unit
29 attachment device for light-emitting fibers to a rod
29' ring of attachment device
A outside
a light-emitting container inner wall section
AE reception entrance of illuminant-receiving pocket
BH container height
BB container width
b light-emitting container inner wall section
c light-emitting rotor blade section
d light-emitting rotor blade section
e light-emitting rotor blade section
E end of illuminant-receiving pocket
G handle
I container inside
L left side
LA longitudinal axis of a light-emitting rod
O upper edge of container
R right side
T pocket inside
TL pocket length
V pocket inner volume

The invention claimed is:

1. A disposable container (1, 1b) of a bioreactor (1a), the disposable container (1, 1b) being designed for filling with a medium (8) that comprises a photoreactive substance, for at least partially triggering at least one photochemical reaction of the photoreactive substance, the disposable container (1, 1b) comprising:

a flexible, transparent plastic material that is configured in one piece to define a container casing (4) that includes:
  a container bottom (1'),
  a container wall (12a) extending up from the container bottom (1') and surrounding a container interior (22), and
  at least one illuminant-receiving pocket (11) that is at least partially transparent for electromagnetic radiation (14), the at least one illuminant-receiving pocket (11) extending from the container wall (12a) into the container interior (22) and forming at least one illuminant opening (12) that is open to an outside (A) of the container casing (4) at the container wall (12a), the at least one illuminant receiving pocket (11) being configured for at least partially receiving at least one illuminant (15, 15a) inserted at least partially into the at least one illuminant-receiving pocket (11) at the at least one illuminant opening (12) in the container wall (12a) of the container casing (4), the at least one illuminant-receiving pocket (11) and the at least one illuminant (15, 15a) projecting substantially horizontally inward of the container wall (12a) and into the container interior (22) when the at least one illuminant (15, 15a) is inserted at least partially into the at least one illuminant-receiving pocket (11), thereby enabling the medium (8) to be irradiated at least partially by the at least one illuminant (15, 15a) such that the photochemical reaction of the photoreactive substance can be triggered by electromagnetic radiation (14) emitted by the at least one illuminant (15, 15a), and the at least one illuminant-receiving pocket (11) hanging down from the container wall (12a) toward the container bottom (1') of the container casing (4) when the at least one illuminant (15, 15a) is not in the at least one illuminant-receiving pocket (11), wherein:

the at least one illuminant (15, 15a) is isolated from the medium (8) by the at least one illuminant-receiving pocket (11);

a stirring shaft (9) spaced inward of the container wall (12);

a rotor blade (5) mounted to the stirring shaft (9); and a further illuminant (15b) extending along the stirring shaft (9) thereby enabling the medium (8) to be irradiated at least partially by the further illuminant (15b).

2. The container (1, 1b) according to claim 1, further comprising a removable container lid and at least one illuminant opening (12b) in the removable container lid.

3. The container (1, 1b) according to claim 1, wherein the container (1, 1b) is sterilizable.

4. The container (1, 1b) according to claim 1, wherein the further illuminant (15b) is wound around the stirring shaft (9).

5. The container (1, 1b) of claim 1, wherein the stirring shaft (9) has a stirring shaft cavity (9a) with an at least partially transparent stirring shaft wall (9b); and the further illuminant (15b) is disposed in the stirring shaft cavity (9a) so that the further illuminant (15) can emit electromagnetic radiation through the stirring shaft wall (9b) into the container interior (22) and can trigger the photochemical reaction of the photoreactive substance of the medium.

6. The container (1, 1b) according to claim 5, wherein the at least one illuminant (15) comprises a light source (15d).

7. The container (1, 1b) according to claim 6, wherein the container casing (4) comprises a container casing inner surface (4a) that comprises a container inner wall structure (17) designed to:

form a surface (27) enlarged with respect to an unstructured smooth container casing inner surface (4a) and to receive at least part of the at least one illuminant (15) on or in the container inner wall structure (17); and or influence a flow profile of a medium in the container interior.

8. The container according to claim 5, wherein the at least one illuminant (15, 15a, 15b) is configured to apply infrared radiation.

9. The container according to claim 5, wherein the stirring element (3) and the container interior (22) are configured to produce a circular flow profile.

10. The container (1, 1b) according to claim 1, wherein the container casing (4) is a flexible bag.

11. The container according to claim 1, wherein the flexible, transparent plastic material is a light-emitting film (15c) that can output or emit electromagnetic radiation (14) to the container interior (22).

* * * * *